United States Patent
Burz et al.

(10) Patent No.: US 8,596,273 B2
(45) Date of Patent: Dec. 3, 2013

(54) RESPIRATORY MASK AND METHOD FOR MANUFACTURING A RESPIRATORY MASK

(75) Inventors: Johann S. Burz, Wielenbach/Wildzhofen (DE); Achim Biener, Aufkirchen (DE); Bernd Christoph Lang, Gräfelfing (DE); Philip Rodney Kwok, Chatswood (AU); Karthikeyan Selvarajan, Gosford (AU); Robert Edward Henry, Roseville (AU)

(73) Assignees: ResMed R&D Germany GmbH, Martinsried (DE); ResMed Limited, Bella Vista (AU)

( * ) Notice: Subject to any disclaimer, the term of this patent is extended or adjusted under 35 U.S.C. 154(b) by 1718 days.

(21) Appl. No.: 11/988,569

(22) PCT Filed: Jul. 19, 2006

(86) PCT No.: PCT/AU2006/001021
§ 371 (c)(1),
(2), (4) Date: Jan. 10, 2008

(87) PCT Pub. No.: WO2007/009182
PCT Pub. Date: Jan. 25, 2007

(65) Prior Publication Data
US 2009/0032024 A1 Feb. 5, 2009

(30) Foreign Application Priority Data
Jul. 19, 2005 (DE) .......................... 10 2005 033 648
Jul. 19, 2005 (DE) .......................... 10 2005 033 650

(51) Int. Cl.
*A61M 16/06* (2006.01)

(52) U.S. Cl.
USPC ............ 128/206.21; 128/206.23; 128/206.24; 128/206.25; 128/206.26; 128/206.28

(58) Field of Classification Search
USPC ............. 128/206.28, 201.17, 204.18, 205.25, 128/205.27, 206.17, 206.12, 206.21, 128/206.24, 207.13
See application file for complete search history.

(56) References Cited

U.S. PATENT DOCUMENTS

| 4,317,788 A | 3/1982 | Imada et al. |
| 4,344,981 A | 8/1982 | Imada et al. |

(Continued)

FOREIGN PATENT DOCUMENTS

| GB | 2 038 703 | 7/1980 |
| GB | 2 397 244 | 7/2004 |

(Continued)

OTHER PUBLICATIONS

Notice of Reasons for Rejection mailed Jun. 12, 2012 in Japanese Appln. No. 2008-521748, with English translation (5 pages).
Examiner's First Report issued Feb. 14, 2011 in Australian Appln. No. 2006272456 (4 pages).
Second Office Action issued Nov. 1, 2011 in Chinese Appln. No. 200680026602.8, with English translation (19 pages).
International Search Report mailed Oct. 30, 2006.

(Continued)

*Primary Examiner* — Clinton T Ostrup
(74) *Attorney, Agent, or Firm* — Nixon & Vanderhye P.C.

(57) ABSTRACT

A respiratory mask, a mould for a respiratory mask, as well as to a method for producing a respiratory mask are disclosed, in which manufacturability and usability of respiratory masks are improved. A respiratory mask is disclosed for administering a breathable gas to a patient, the respiratory mask comprising a first component formed from a flexible material and a second component formed from a material that is more rigid than the flexible material, wherein the first component is formed onto the second component by an overmoulding process.

29 Claims, 34 Drawing Sheets

(56) References Cited

U.S. PATENT DOCUMENTS

| | | | |
|---|---|---|---|
| 5,102,365 A * | 4/1992 | Wang | 446/221 |
| 5,391,248 A | 2/1995 | Brain | |
| 5,676,133 A * | 10/1997 | Hickle et al. | 128/205.12 |
| 6,196,223 B1 * | 3/2001 | Belfer et al. | 128/206.25 |
| 6,397,847 B1 | 6/2002 | Scarberry | |
| 6,409,954 B1 | 6/2002 | Mulligan | |
| 6,532,961 B1 * | 3/2003 | Kwok et al. | 128/206.21 |
| 6,773,776 B2 | 8/2004 | Gust | |
| 6,902,812 B2 | 6/2005 | Valint, Jr. et al. | |
| 2002/0029780 A1 * | 3/2002 | Frater et al. | 128/206.24 |
| 2002/0100479 A1 | 8/2002 | Scarberry et al. | |
| 2003/0075180 A1 | 4/2003 | Raje et al. | |
| 2005/0172969 A1 | 8/2005 | Ging et al. | |
| 2005/0199239 A1 * | 9/2005 | Lang et al. | 128/206.24 |

FOREIGN PATENT DOCUMENTS

| | | |
|---|---|---|
| JP | 63-29654 A | 2/1988 |
| JP | 11-508159 A | 7/1999 |
| JP | 2004-505686 A | 2/2004 |
| JP | 2004-526464 A | 9/2004 |
| WO | WO 97/00092 A1 | 1/1997 |
| WO | 02/13884 | 2/2002 |
| WO | WO 02/11804 A2 | 2/2002 |
| WO | 03/016018 | 2/2003 |
| WO | WO 03016018 A1 * | 2/2003 |
| WO | 03/035156 | 5/2003 |
| WO | WO 03105921 A2 * | 12/2003 |

OTHER PUBLICATIONS

International Application No. PCT/EP02/11798 filed May 1, 2003 (p. 1 of the Specification, publication No. WO 03/035156.
U.S. Appl. No. 60/682,827, filed May 23, 2005 (p. 23 of specification).
U.S. Appl. No. 60/734,282, filed Nov. 8, 2005 (p. 23 of specification).
U.S. Appl. No. 60/758,200, filed Jan. 12, 2006 (p. 27 of specification).
U.S. Appl. No. 10/533,940, filed Dec. 29, 2006 (p. 32 of specification, not yet published).
U.S. Appl. No. 10/027,689, filed Jan. 3, 2005 (p. 33 of specification, published No. U.S. 2005/0172969).
Chinese Office Action and English Translation for corresponding Chinese Appln. No. 2011031100641830, mailed issued Mar. 16, 2011 (14 pages).
European Patent Office Communication mailed Apr. 3, 2012 in EP Application No. 06 760 882.8 (5 pages).
Decision of Rejection issued Apr. 19, 2012 in Chinese Appln. No. 200680026602.8, with English translation (22 pages).
Notice of Reasons for Rejection Mailed Jul. 26, 2011 in Japanese Appln. No. 2008-521748, with English Translation (5 pages).
Supplementary European Search Report for co-pending European Application No. 06760882, mailed Feb. 22, 2010, 8 pages.
Notice of Reasons for Rejection mailed Mar. 19, 2013 in Japanese Application No. 2008-521748, with English Translation (5 pages).
Patent Examination Report No. 1 issued Jan. 21, 2013 in Australian Application No. 2012244359 (5 pages).

* cited by examiner

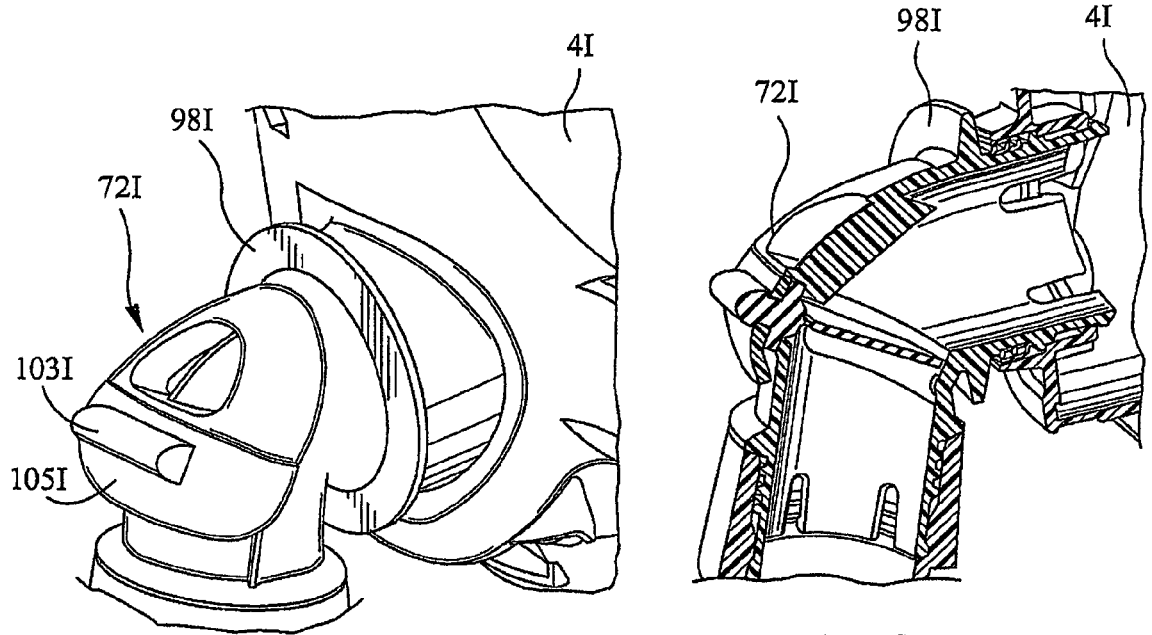
FIG. 13
FIG. 14
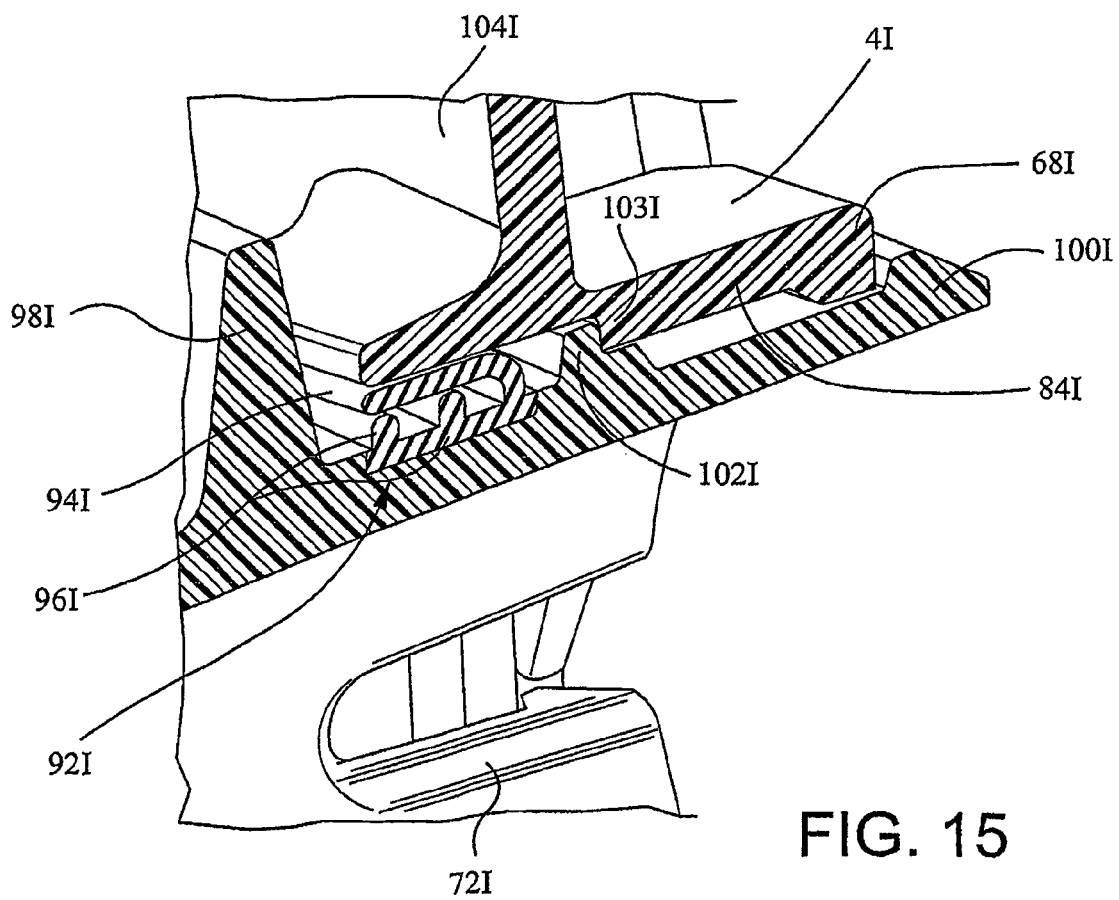
FIG. 15

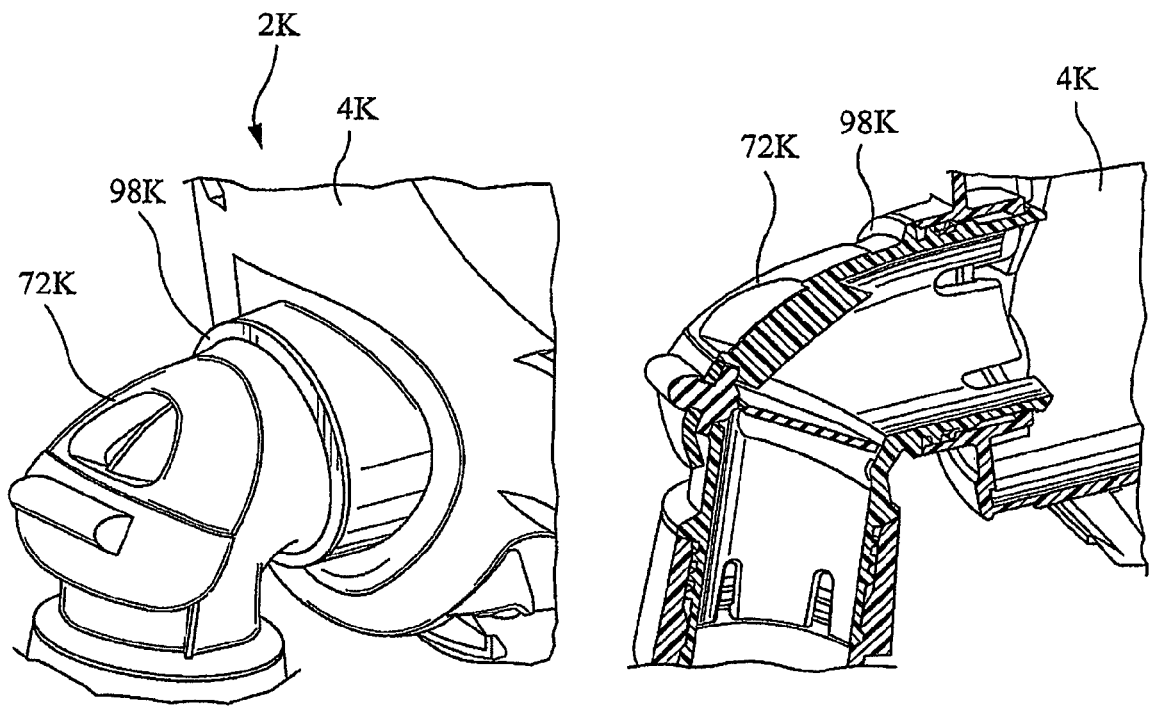
FIG. 20
FIG. 21
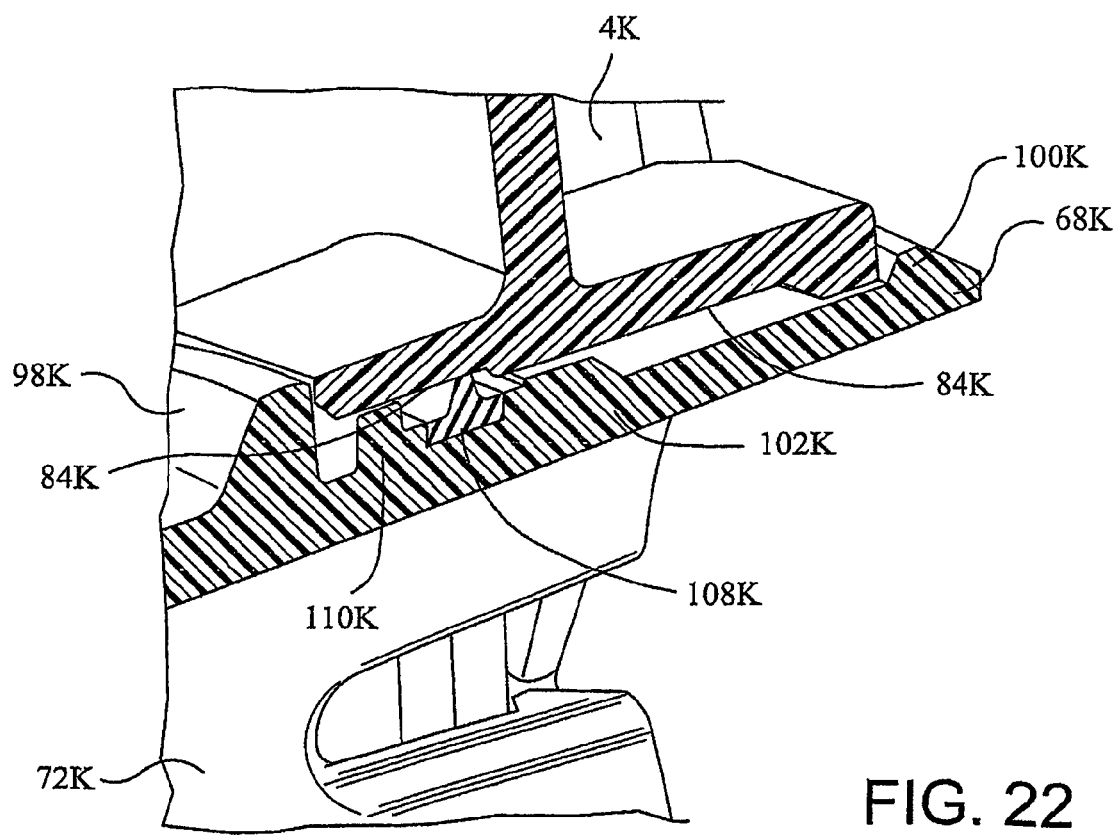
FIG. 22

RESPIRATORY MASK AND METHOD FOR MANUFACTURING A RESPIRATORY MASK

This application is the U.S. national phase of International Application No. PCT/AU2006/001021, filed 19 Jul. 2006, which designated the U.S. and claims priority to German Application Nos. 10 2005 033650.7, filed 19 Jul. 2005, and 10 2005 033648.5, filed 19 Jul. 2005, the entire contents of each of which are hereby incorporated by reference.

CROSS-REFERENCES TO RELATED APPLICATIONS

This application claims the benefit of German Patent Application Nos. 10 2005 033 648.5 and 10 2005 033 650.7, each filed Jul. 19, 2005 and incorporated herein by reference in its entirety.

BACKGROUND OF THE INVENTION

1. Technical Field

The invention relates to respiratory masks and manufacturing processes for respiratory masks. In particular, the invention relates to overmoulding portions of respiratory masks.

It should be noted that the phrase "respiratory mask" in this specification includes any type of patient interface, including full face masks, nasal masks, and nasal prong masks etc.

2. Introduction to Respiratory Masks

Respiratory masks are used for administering a breathable gas, such as ambient air, at a pressure that is, at least sometimes, above the ambient pressure. This is known as Positive Airway Pressure (PAP) therapy, such as Continuous Positive Airway Pressure (CPAP) or Variable Positive Airway Pressure (VPAP) therapy, and may be used for treating Sleep Disordered Breathing (SDB) or other medical conditions.

International Patent Application PCT/EP02/11798, filed by Medizintechnik fur Arzt und Patient (MAP), now ResMed Germany, discloses a respiratory mask for administering a breathable gas to a user. This respiratory mask makes it possible, when worn by a user, to seal off an interior volume of the respiratory mask from the environment. Such respiratory masks are used particularly in conjunction with medical or therapeutic administration of breathable gases (and additions thereto, such as drug vapours), as well as in the industrial field, for instance in the field of gas masks and breathing equipment. Typically, the interior volume is sealed using a sealing cushion or lip structure that is inwardly curved and extends around an opening in the mask and seals against the user's face. Sealing cushions are generally made from an elastically deformable material, such as silicone and seal by compression against the user's face. The level of sealing achieved generally increases with the contact pressure of the sealing cushion against the face.

2.1 Manual Labour

It is known amongst skilled persons that conventional mask systems are difficult to assemble. Consequently, assembly of components requires significant labour time, particularly while assemblers are learning. Further labour is required to check the correct assembly of mask components. Manual labour increases the cost of goods and subsequently may decrease the profitability of respiratory mask manufacturers and/or make masks more expensive for patients.

Automation of the manufacturing assembly process by using robotics, for example, is difficult due to the often complex manipulations required to assemble mask components. It is also known that flexible components, as are common in masks and mask systems, are exceedingly difficult to handle robotically. For automation to be achieved a very high level of robotic dexterity would be required and the expense of designing, manufacturing and configuring such robotics has generally been considered prohibitive.

2.2 Moulding

In general terms, the greater the number of components a mask includes, the more expensive it is to manufacture because more component moulds are required.

2.3 Assembly by Patients

Assembly and disassembly of mask components by patients can be difficult (e.g. after washing the mask prior to use). This problem is often exacerbated by the often relatively low dexterity of patient's suffering from sleep disordered breathing (e.g. because of age, weight or arthritis). Generally, therefore, the more components a mask has, the more difficult it is for patients to assemble. Furthermore, the higher the number of mask components, the greater the risk of those components getting lost and the greater the risk of mis-assembly.

2.4 Biological Contamination

Another problem with masks assembled from components that can be separated by a user is the build-up of biological contaminants in the crevices between the components, even when the mask is being regularly washed.

2.5 Mask Comfort

One ongoing problem encountered in mask design is the difficulty associated with creating a comfortable mask. Ordinary silicone membrane sealing technology can feel unpleasant and sometimes lead to pressure sores when the mask in tightened too much for an extended period of time.

2.6 Mask Aesthetics

It is known that good mask aesthetics can be achieved by a sleek, simple design that does not have a 'busy' appearance. However, the various functional requirements of masks sometimes impinges on a designers ability to design a mask with good aesthetics. This problem can be compounded when masks are made from a relatively large number of components that do not connect in a smooth, contoured fashion.

BRIEF SUMMARY OF THE INVENTION

3.0 Embodiments of the Present Invention

Embodiments of the present invention seek to address one or more of the abovementioned problems or to at least provide a commercially valuable alternative.

One aspect of the invention relates to a method for manufacturing a respiratory mask wherein at least one step in the manufacturing process is the integral forming of at least two components in or from at least two different materials. Another aspect of the invention relates to a respiratory mask manufactured by the above method.

Preferably, the integral forming is an overmoulding operation which is automated, for example, by using robotics. Overmoulding may be performed by any known moulding technique, including surface treatment by any known treatment, such as plasma treatment. An overmoulding step may be used to mould a flexible component onto a component that is less flexible than the flexible material (henceforth a "substantially rigid component"). In one embodiment, the mask cushion (e.g., silicone) and frame (e.g., polycarbonate) are co-moulded using one of the manufacturing processes described herein.

As a result, it advantageously becomes possible to create a respiratory mask in which relatively complex geometries of the flexible components and of the substantially rigid components coupled to them can be realized. Furthermore, the relatively time-consuming and labour intensive mask manufacturing process can now be either partially or completely automated. This advantage arises because one or more mask assembly steps and mask components may not be required because two components (e.g. cushion and frame) are joined during moulding and so do not require subsequent assembly.

In an especially preferred embodiment of the invention, the integral forming of a flexible component onto a substantially rigid component is done directly in an injection moulding tool. This injection moulding tool preferably includes multiple cavities.

A liquid silicone rubber (LSR) material is preferably used for the flexible material and a polycarbonate plastic is preferably used for the substantially rigid material. In an especially preferred embodiment of the invention, the integral forming of the components is carried out in such a way that the flexible component can be manually separated from the substantially rigid component. This allows the flexible component to be removed as required. It is also possible to accomplish the integral forming such that the flexible component is coupled with the substantially rigid component in an intimately adhering way (i.e. the components cannot be manually separated).

In an especially preferred embodiment of the invention, at least one of the flexible components of the respiratory mask is a sealing cushion. The sealing cushion is preferably integrally formed onto the substantially rigid component in such a way that an intimate adhesive bond results. The bonding geometries of the substantially rigid component and the flexible components as well as other factors may be manipulated to provide a required level of adhesion.

According to another embodiment of the invention, there is provided a respiratory mask for administering a breathable gas to a patient, the respiratory mask comprising a) a first component formed from an elastomeric material; and b) a second component formed from a material that is less flexible than the elastomeric material, wherein the first component is integrally formed onto the second component.

According to another embodiment of the invention, there is provided a respiratory mask comprising a substrate made of a relatively rigid material, wherein the substrate includes at least one treated portion inclined to accept a reactive substance; and an elastomer that is made of a relatively more flexible material compared to the relatively rigid material of the substrate, said elastomer being applied to the substrate and secured to the substrate via an induced adhesive bond formed between said treated portion and a surface of the elastomer abutting the treated portion.

According to another embodiment of the invention, there is provided a method for manufacturing a respiratory mask, comprising: providing an elastomeric material for forming into a first component; providing a second component that is less flexible than the elastomeric material in a mould; and integrally forming the elastomeric material onto the second component within the mould in order to form the first component.

The first component can be manually separated from the second component, or the first component is joined to the second component in an intimately adhering manner. The method may further comprise pre-treating the second component to strengthen adhesion between the first and second components. The pre-treating step may comprise applying plasma, preferably an atmospheric gas plasma, to a bonding surface of the second component. Corona treatment is an alternative. The integral forming may be carried out in an injection moulding tool.

According to another embodiment of the invention, there is provided a mould for a respiratory mask for administering a breathable gas to a patient, the respiratory mask comprising a first component formed from an elastomeric material; and a second component formed from a material that is less flexible than the elastomeric material, wherein the first component is integrally formed onto the second component, wherein the mould comprises a mould cavity in which the first component is moulded onto the second component.

According to another embodiment of the invention, there is provided a method for manufacturing a respiratory mask comprising forming a substrate made of a relatively rigid material; and overmoulding an elastomer to or with the substrate, wherein the mask includes a mask frame and an elbow provided to the frame, and wherein the elbow or frame includes at least one selected portion including said substrate, and the method further comprises overmoulding said elastomer onto the selected portion.

According to another embodiment of the invention, there is provided a method for manufacturing a respiratory mask comprising forming a substrate made of a relatively rigid material; and overmoulding an elastomer to or with the substrate, wherein the mask includes a mask frame, a cushion provided to the frame and a forehead support positioned above the frame, wherein the mask comprises a flexible portion coupling the frame and the forehead support, the flexible portion including a structural member including said substrate and at least one disc or tube including said elastomer.

According to another embodiment of the invention, there is provided a method for manufacturing a respiratory mask comprising forming a substrate made of a relatively rigid material; and overmoulding an elastomer to or with the substrate, wherein the mask includes a mask frame made at least in part from said elastomer and a retaining ring including said substrate, wherein the method further includes overmoulding the frame onto the ring.

According to another embodiment of the invention, there is provided a method for manufacturing a respiratory mask comprising forming a substrate made of a relatively rigid material; and overmoulding an elastomer to or with the substrate, wherein the mask comprises a frame and a cushion and a headgear assembly to support the frame and cushion, wherein the headgear assembly includes a yoke associated with a strap and a seal ring provided to the yoke, wherein the yoke includes at least one selected portion including the substrate and the method comprises co-moulding the seal ring onto the yoke.

According to another embodiment of the invention, there is provided a method for manufacturing a respiratory mask comprising forming a substrate made of a relatively rigid material; and overmoulding an elastomer to or with the substrate, wherein the mask includes a frame and a gas washout vent having at least one hole or pore, wherein the frame includes at least one selected portion including the substrate and the method comprises co-moulding the gas washout vent onto the frame.

According to another embodiment of the invention, there is provided a method for manufacturing a respiratory mask comprising forming a substrate made of a relatively rigid material; and overmoulding an elastomer to or with the substrate, wherein the mask includes a frame having an aperture and a plug provided to close the aperture, the frame including at least a selected portion including said substrate and the method comprise overmoulding the plug onto the frame.

According to another embodiment of the invention, there is provided a method for manufacturing a respiratory mask comprising forming a substrate made of a relatively rigid material; and overmoulding an elastomer to or with the substrate, wherein the mask includes a conduit including said substrate and a wall member formed at least in part by said elastomer, and said method further comprises overmoulding the wall member and the reinforcement member.

According to another embodiment of the invention, there is provided a method for manufacturing a respiratory mask comprising forming a substrate made of a relatively rigid material; and overmoulding an elastomer to or with the substrate, wherein the frame includes a port portion and a port cap provided to the frame, wherein the port portion includes at least a selected portion including the substrate and the method further comprises overmoulding the port cap onto the frame.

According to another embodiment of the invention, there is provided a method for manufacturing a respiratory mask comprising forming a substrate made of a relatively rigid material; and overmoulding an elastomer to or with the substrate, wherein said mask includes a frame with said substrate and a bladder is provided to the frame and formed at least in part from said elastomer.

According to another embodiment of the invention, there is provided a method for manufacturing a respiratory mask comprising forming a substrate made of a relatively rigid material; and overmoulding an elastomer to or with the substrate, wherein the mask includes a frame including at least one port, and nasal cannulae, wherein the frame includes said substrate and the cannulae are formed at least in part from the elastomer, the cannulae being in communication with the port.

According to another embodiment of the invention, there is provided a method for manufacturing a respiratory mask comprising forming a substrate made of a relatively rigid material; and overmoulding an elastomer to or with the substrate, wherein the mask includes a frame, a cushion, a forehead support positioned above the frame, and a forehead pad provided to the forehead support, the forehead pad including said elastomer and the forehead support including said substrate.

According to another embodiment of the invention, there is provided a method for manufacturing a respiratory mask comprising forming a substrate made of a relatively rigid material; and overmoulding an elastomer to or with the substrate, wherein the mask includes a mask frame including the substrate and a mask cushion including the elastomer, wherein the frame includes a peripheral region and the cushion includes a T-shaped or L-shaped rim overmoulded to the frame.

According to another embodiment of the invention, there is provided a method for manufacturing a respiratory mask comprising forming a substrate made of a relatively rigid material; and overmoulding an elastomer to or with the substrate, wherein the mask includes a mask frame including the substrate and a mask cushion including the elastomer, in which the mask frame and the mask cushion form at least one of a diagonal joint, a lap joint and/or a V-joint.

According to another embodiment of the invention, there is provided a method for manufacturing a respiratory mask comprising forming a substrate made of a relatively rigid material; and overmoulding an elastomer to or with the substrate, wherein the mask includes a frame and a cushion, the cushion having an expandable bladder having an interior defined by an interior surface of the elastomer and a portion of the frame that is not treated, and the frame includes a port to allow introduction of a substance delivered to the interior to expand the bladder.

According to another embodiment of the invention, there is provided a method for manufacturing a respiratory mask comprising forming a substrate made of a relatively rigid material; and overmoulding an elastomer to or with the substrate, wherein the mask includes a mask frame a cushion and a cushion clip to secure the cushion to the frame, wherein the substrate is provided as part of the cushion clip and the cushion includes the elastomer.

According to another embodiment of the invention, there is provided a humidifier tub for a flow generator comprising a substrate made of a relatively rigid material, wherein the substrate includes at least one treated portion inclined to accept a reactive substance; and an elastomer that is made of a relatively more flexible material compared to the relatively rigid material of the substrate, said elastomer being applied to the substrate and secured to the substrate via an induced adhesive bond formed between said treated portion and a surface of the elastomer abutting the treated portion wherein the humidifier tub includes a lid having said substrate and a seal made in part from said elastomer.

According to another embodiment of the invention, there is provided a method for manufacturing a humidifier tub comprising forming a substrate made of a relatively rigid material; and overmoulding an elastomer to or with the substrate, wherein the humidifier tub includes a lid having said substrate and a seal made in part from said elastomer.

According to another embodiment of the invention, there is provided a humidifier tub comprising a substrate made of a relatively rigid material; and an elastomer overmoulded with or to the substrate, wherein the humidifier tub includes a lid having said substrate and a seal made in part from said elastomer.

These and other aspects will be described in or otherwise apparent from the following detailed description of embodiments.

BRIEF DESCRIPTION OF THE DRAWINGS

Embodiments of the invention will now be described with reference to the accompanying exemplary drawings, in which:

FIG. 13 is a perspective view of a portion of a respiratory mask frame and elbow according to a eighth embodiment of the present invention;

FIG. 14 is a perspective, cross-sectional view of the portion of the frame and elbow of FIG. 13;

FIG. 15 is an enlarged, perspective, cross-sectional view of the frame and elbow of FIG. 13 illustrating the elbow sealing arrangement;

FIG. 20 is a perspective view of a portion of a respiratory mask frame and elbow according to an tenth embodiment of the present invention;

FIG. 21 is a perspective, cross-sectional view of the portion of the frame and elbow of FIG. 20;

FIG. 22 is an enlarged, perspective, cross-sectional view of the frame and elbow of FIG. 20 illustrating the elbow sealing arrangement;

Figure 1:
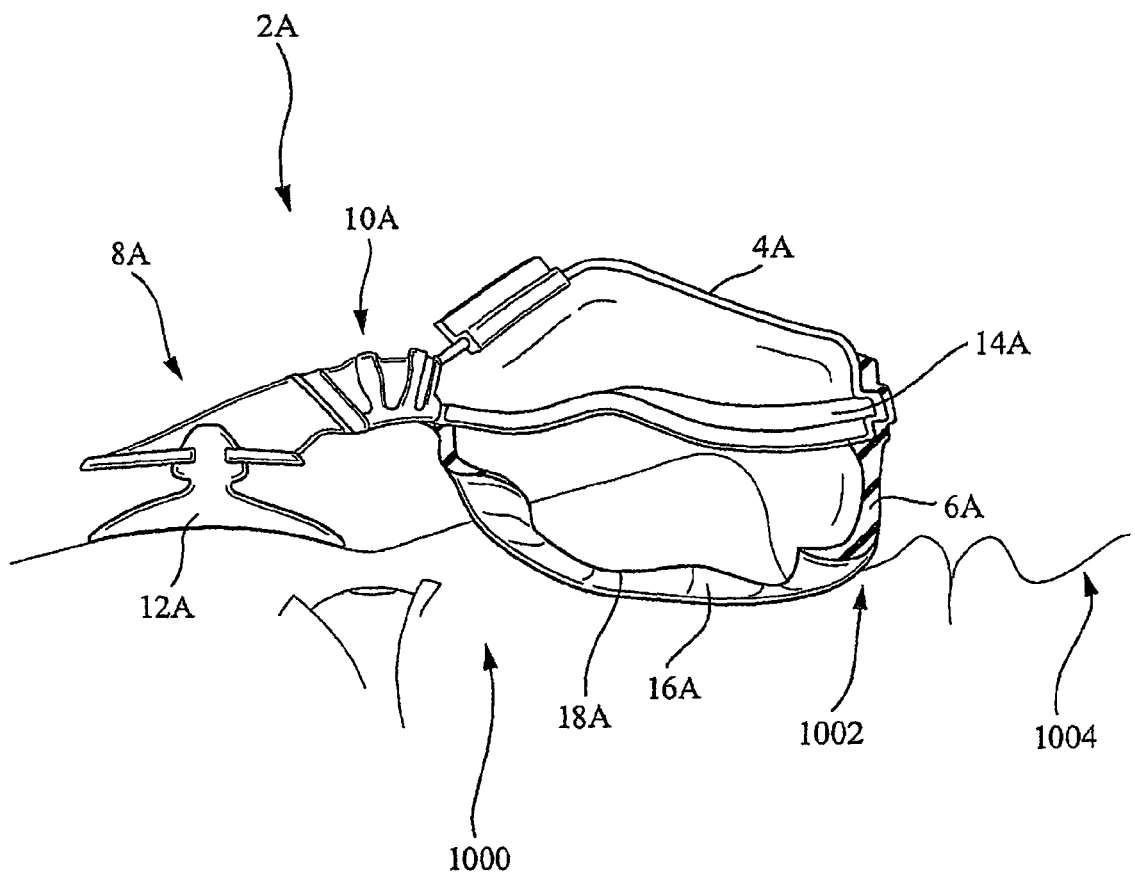
FIG. 1 is a side, partial cross-sectional view of a respiratory mask according to a first embodiment of the present invention shown in situ on a patient's face.

DETAILED DESCRIPTION OF ILLUSTRATED EMBODIMENTS OF THE INVENTION 5.0 Introduction
5.0.1 Definitions
5.0.1.1 "Overmoulding"

The word "overmoulding" is used in this specification in its broadest sense, that is, in the sense of moulding one component onto another component, or integrally forming two components. A number of different moulding processes that are deemed to fall within the ambit of the word 'overmoulding' as used in this specification are described below. It should be appreciated that this group of moulding processes is inclusive and not exhaustive.

Overmoulding is used to refer to the process of forming a bond between a first material, known as the "substrate material", and a second material known as the "overmould". However, the word 'overmoulding' also refers to moulding where no bond or substantive bond is formed but where respective components are held together, for example, only by a mechanical interlocking, keying or undercut. Mechanical interlocking can be either macroscopic (e.g., undercuts) or microscopic (e.g., depending on abrasion of the substrate).

The word 'overmoulding' also refers to a type of moulding where the two materials to be joined are inserted into the mould at the same time or at two points in time close together. For example, overmoulding includes "overmoulding" or "co-injection moulding". A co-injection moulding process involves a first step where a first component (e.g., substrate) is moulded in a first mould and once ejected progresses to a second step where the first component is placed inside a second mould for the moulding of a second component (e.g., elastomer) on to it. In between the moulding steps, the first component may be treated to more readily accept a reactive substance. Treatment may take the form of plasma treatment, for example, and this treatment may take place within the mould(s) or outside the moulds. What distinguishes co-injection moulding from other types of overmoulding is that when the first component is being progressed through the second step another first component is being manufactured by the first step. That is, the first and second steps are being performed simultaneously for sequentially manufactured products. This can be achieved with a rotating tool set (e.g., a turntable with two or more moulding stations) or robotic arm.

'Overmoulding' also refers to "Moving Cores Moulding" where one injection moulding machine fitted with two injection systems is used. Once the substrate has cooled sufficiently a section of the tool retracts, forming a cavity for the overmould material. Moving cores have conventionally been best suited to simple overmoulds, where a uniform thickness of overmould is required.

"Rotating Platen or Stripper Plate" moulding is also considered a overmoulding process. This process involves rotation of the tool once the substrate has cooled. A rotating platen rotates the component on its core, whereas a rotating stripper plate lifts the component off its core before rotating. The main advantage of these methods is that they allow a different shaped cavity or core to be used to form the overmould. More sophisticated components can be created using this method.

5.0.1.2 "Flexible Material/Component"

The words "flexible material/component" as used in this specification include any material with physical properties similar to or the same as an elastomer material which is defined in the Webster's New World Dictionary as, "a rubber-like synthetic polymer, as silicone rubber". Therefore, a rubber, a natural polymer or any other rubber-like material including some gels are included within the scope of the words "flexible material/component".

The words "flexible material/component" also refer to various mixtures of individual elastomer components. These elastomers may be pre-mixed or mixed in the mould. Examples of elastomers are liquid silicone rubber (LSR), solid silicone rubber and thermoplastic elastomers (TPEs).

5.01.3 "Substantially Rigid Component"

A substantially rigid component includes all materials that are less flexible than the flexible material. Examples of substantially rigid components are polycarbonate (e.g. Lexan) and phenol formaldehyde (e.g. Bakelite.)

5.0.2 Bonding

There are 2 main types of bond: adhesive (an interfacial property) & cohesive (a bulk property). This application is largely concerned with the former rather than the latter.

There are several different types of adhesive bonding:
  adsorption bonding depends on intermolecular attractive forces between adhesive and substrate (e.g. Van der Waals forces)
  chemical bonding depends on available functional groups on the substrate surface and their reactivity with the molecules of the adhesive. Also known as covalent bonding.
  diffusion bonding depends on the mutual solubility between the substrate and adhesive
  electrostatic bonding depends (typically for solids) on dipole-dipole interactions.

Ideally, the adhesive strength of the bond formed in embodiments of the invention is significantly greater than the cohesive strengths of the components thereof. The level of adhesion achievable is dependant on the preparation of the bonding surface areas, amongst other factors. A pretreatment may be applied to a selected bonding area of the substantially rigid component to enhance adhesion.

One such pretreatment is the application of plasma, such as an atmospheric gas plasma, to the bonding area of the substrate. Plasma treatment chemically activates the bonding area to enhance chemical bonding. Plasma treatment is effected by blasting highly energized gases at the surface which causes reactive molecules to be embedded in the surface. These molecules form a bond with the relatively rigid component, e.g., in the case of silicone, a polydimethyl siloxane bond may be formed. The gas is typically compressed air, but it can be nitrogen or other gases. It should be noted that the longer a plasma treated surface is left before bonding, the less effective the treatment will be. Plasma treatment is described in "Plasma Processes and Polymers" by d'Agostino et al., published by Wiley, 2005.

One method of applying plasma treatment is to position a masking sheet or stencil over the surface to which the plasma is to be applied. One or more aperture(s) in the stencil allows the plasma to contact the portion of the surface to be bonded but masks the remainder of the surface. An alternative to use of a masking sheet is the use of a finely controllable plasma gun (e.g. a gun mounted on an apparatus controllable by a computer such as a robotic arm).

Examples of commercially available atmospheric gas plasma guns include Atomflo™ by Surfx Technologies LLC of USA and PlasmaTEC™ by Dyne Technology Ltd of UK.

One alternative to plasma treatment is corona treatment, which typically is a stronger treatment which requires more energy and affects the substrate differently.

A further alternative to plasma treatment is chemically treating the surface by, for example, the application of adhesion promoters, such as silane coupling agents. Another chemical pre-treatment is the application of a solvent to the surface.

Yet another alternative is to use self-adhesive elastomeric material and to apply a non-bonding material (e.g. silicone grease) or contaminant, where a bond is not desired.

A further variation is flame oxidization of the surface.

Advantageously, all these pre-treatment processes allow treatment of only selected areas as required, by masking or otherwise avoiding areas where bonding is not desired.

Adhesion strength is also dependant on timing. A better bond may be formed when the second component is moulded onto the first component if the temperature of the first component is still raised. In the case that a chemical bond is not required, temperature differences and the resulting shrinkage differential may improve mechanical interlocking.

Often when an overmoulding process is used, the substantially rigid component will be moulded with a slight recess around the periphery of the bonding area to assist bonding with the flexible material by providing a level of mechanical interlocking as well as a larger bonding area. Furthermore, bonding along multiple planes with respect to forces applied may assist in reducing adhesive failure.

5.1 General Structure of a Respiratory Mask

A respiratory mask 2A is shown in FIG. 1 in situ on the face of a user 1000. The mask 2A comprises a frame 4A, formed from a substantially rigid component, such as a polycarbonate material, a sealing cushion 6A formed from an elastomeric material, such as liquid silicone rubber (LSR), and a forehead support 8A, which is adjustably coupled to the frame 4A via a flexible portion 10A. The forehead support 8A includes a forehead pad 12A, made from an elastomeric material.

5.2 Sealing Cushion

The cushion 6A has been co-moulded onto a peripheral portion 14A of the frame 4A. In this example, the frame 4A was pretreated such that the cushion 6A forms a high-strength adhesive bond with the frame 4A.

The cushion 6A includes a lip 16A that is curved inwardly and terminates in an aperture 18A that is sized and shaped for receiving at least part of the nose of a patient. The lip 16A traverses an upper lip region 1002 of the user 1000 in the case that the mask 2A is configured as a nasal mask or a chin region 1004 of the user 1000 in the case that the mask 2A is configured as a full-face mask. Although the mask 2A only incorporates a single lip 16A, it should be appreciated that multiple lips could be incorporated. Gel structure(s) may also be incorporated into lip 16A, or in the case that multiple lips are provided into each lip. Alternatively, the lip 16A could be replaced with one or more gel structures.

Moulding the cushion 6A to the frame 4A eliminates the need for a cushion-to-frame securing component and the associated assembly step. This reduces the cost of goods and/or may assist in improving compliance with therapy.

5.2.1 Bonding Configurations

Figure 2:
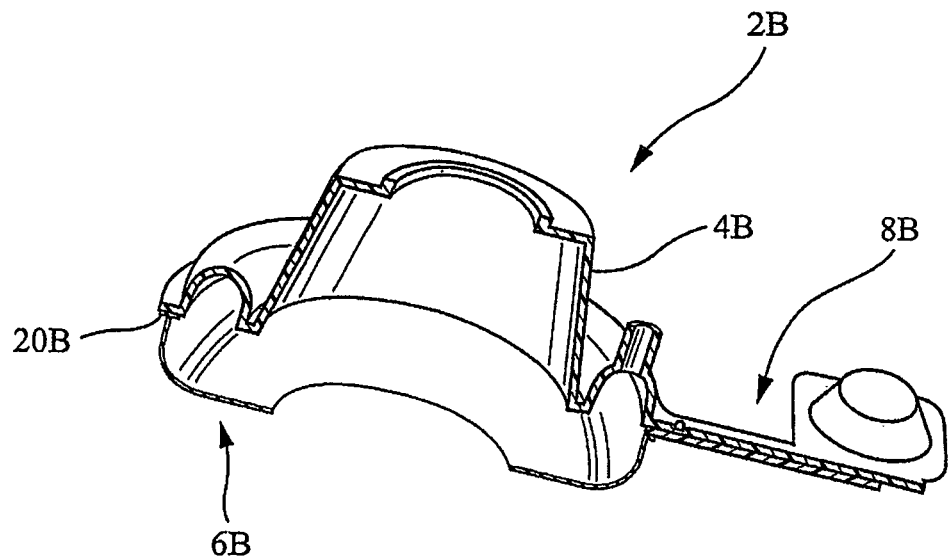
FIG. 2 is a cross-sectional perspective view of a respiratory mask according to a second embodiment of the present invention.
Figure 3:
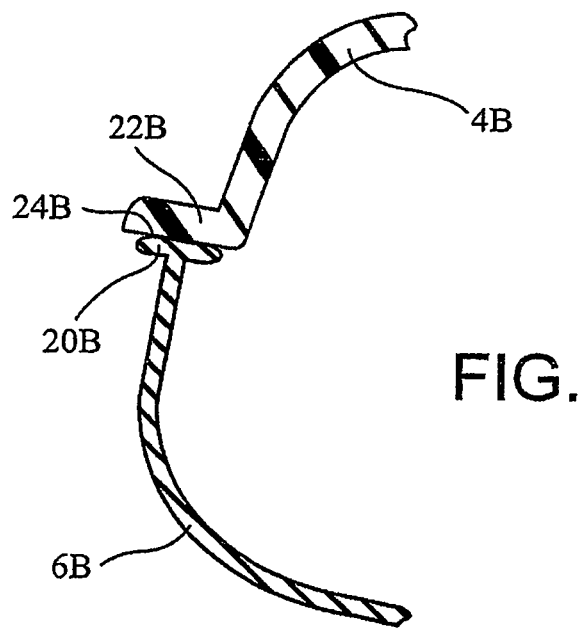
FIG. 3 is a cross-sectional perspective view of an enlarged portion of the frame/cushion interface of the respiratory mask of FIG. 2 and illustrates the bonding configuration therebetween.

Various bond configurations are possible. In one embodiment, shown in FIGS. 2 and 3, the cushion 6B of a respiratory mask 2B has a T-shaped rim 20B that is sized to be bonded to a peripheral region 22B of the frame 4B. The T-shaped rim 20B provides a bonding surface 24B that is larger than it would otherwise be if no T-shaped bonding rim 20B was provided. This larger bonding surface 24B allows a stronger bond to form. Alternatively, an L-shaped bonding rim could be provided. However, the T-shaped bonding rim 20B is advantageous with respect to the L-shaped rim because when the cushion 6B is pulled away from the frame 4B, no bending moment is created. A bending moment could assist a tear developing through the bond. Other suitable bonding configurations include a diagonal joint, a lap joint and a V-joint. Furthermore, the bonding could occur on an interior surface of frame 4B, e.g., a lap joint.

5.2.2 Bonding to Form Bladders

Figure 4:
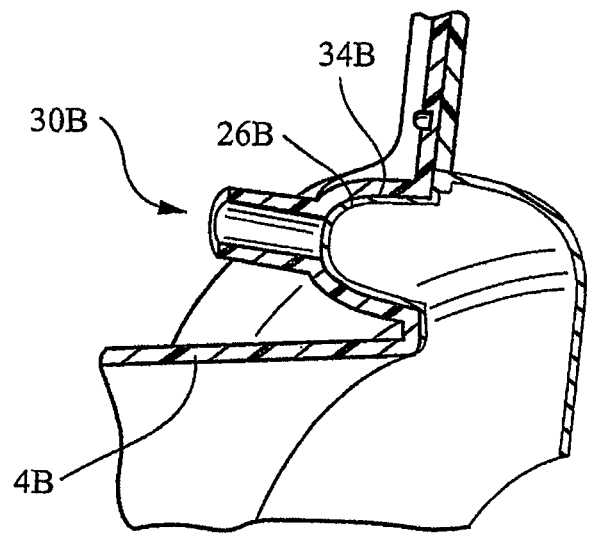
FIG. 4 is a cross-sectional perspective view of an enlarged portion of the frame of the respiratory mask of FIG. 2 and illustrates an elastomer component disposed over and bonded around a peripheral frame channel and in an inwardly disposed configuration.
Figure 5:
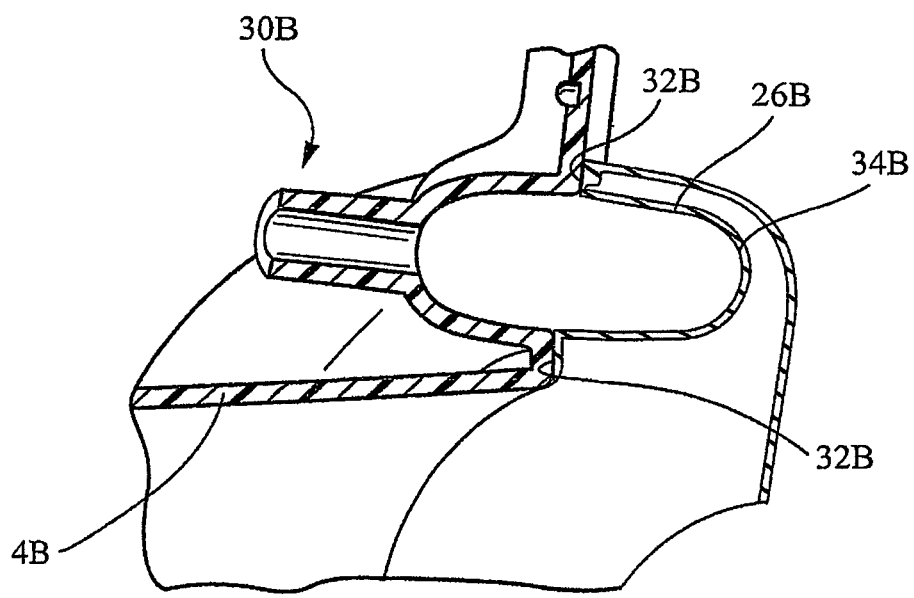
FIG. 5 is a cross-sectional perspective view of an enlarged portion of the frame of the respiratory mask of FIG. 4 and illustrates the elastomer component in an outwardly disposed configuration.

Referring to FIGS. 4 and 5, selective bonding can be utilized to form a bladder 26B that can be expanded. The bladder 26B can be expanded by delivery of pressurized air to a port 30B. The stenciling or masking procedure described in Section 5.0.2 may be utilized to chemically activate bonding areas 32B where sides of the wall 34B of the bladder 26B join the frame 4B. The bonding areas 32B adhere to the portions of the cushion in contact with the bonding areas, while the surface of the bladder 26B is free to separate from the frame 4B since those portions of the frame have not been treated. The pressurized air may be pressurized to 2 bar or any other suitable pressure. Furthermore, gases other than normal air could be used to pressurize the bladder 26B. Alternatively, a gel, foam, liquid or other soft substance may be inserted into the bladder 26B instead of a gas, such that a soft, flexible pad is formed. The pad may be filled and permanently sealed or be releasably or temporarily sealed. The inside surfaces of the pad may be provided with a permeation-resistant liner.

In one embodiment, the gel cushion could be provided using a skin made of LSR that is filled with a gel, e.g., silicone. To prevent the gel from permeating through the LSR skin, the inside surface of the skin could be coated with a liner, such as polyester and/or polyurethane. The liner could be applied using any number of techniques, e.g., spraying (just before the gel is introduced, e.g., in FIG. 5), co-moulding, dipping, brushing, etc.

Figure 6:
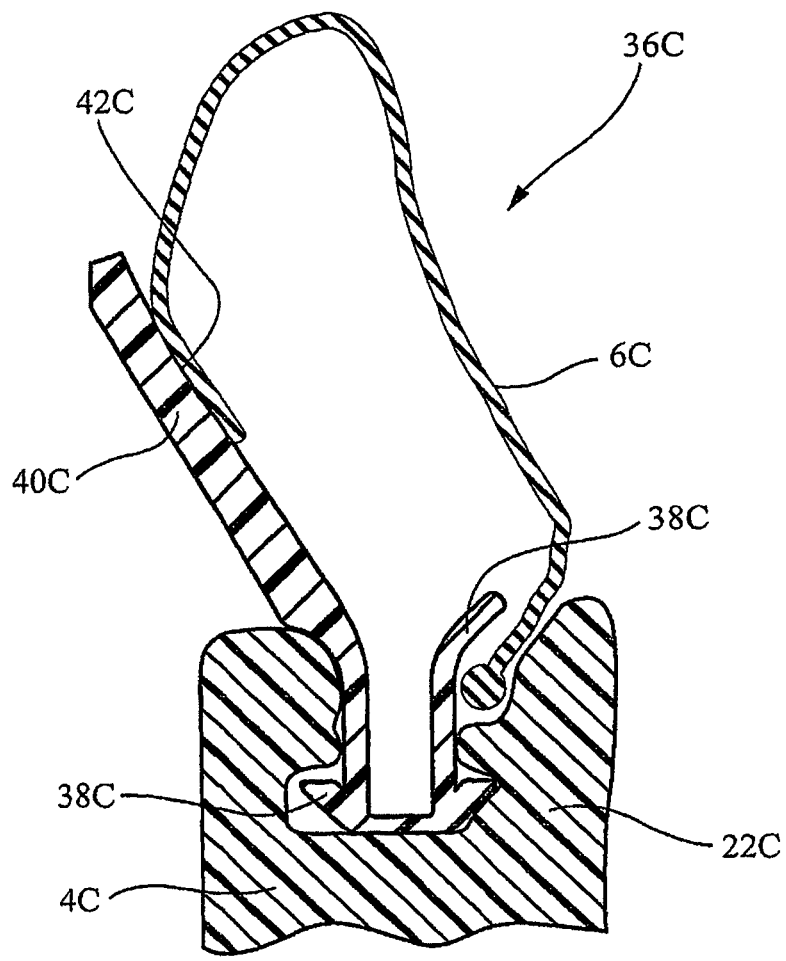
FIG. 6 is a schematic, side, cross-sectional view of a cushion to frame connection according to a third embodiment of the present invention.

Referring to FIG. 6, an alternative reinforced bladder arrangement 36C is shown. In this arrangement the cushion 6C is not directly formed onto the frame 4C but is co-moulded to a clip 38C. The clip 38C is attachable to the frame 4C by a mechanical interlock. The cushion 6C may also be bonded to the clip 38C in a manner such that when attached to the frame 4C, a portion of the cushion 6C is sandwiched between the frame 4C and clip 38C providing a mechanical interlock. The clip 38C is configured with a reinforcing member 40C for supporting and stabilizing an under surface 42C of the cushion 6C. This limits rotation/movement of the cushion 6C on the face of the user.

5.3 Forehead Support

Figure 7:
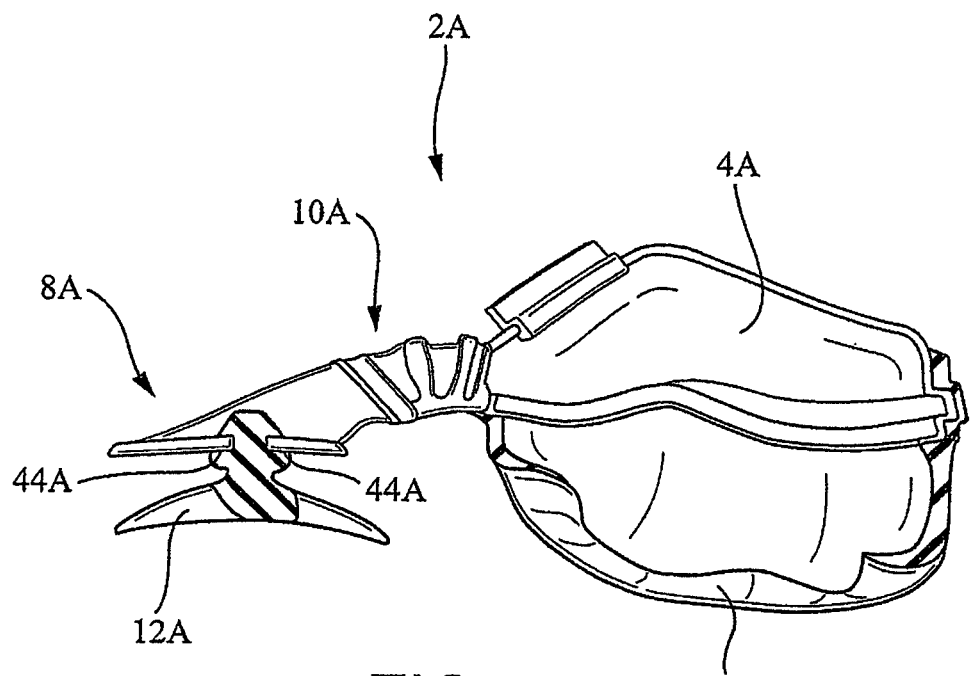
FIG. 7 is a side, partial cross-sectional view of the respiratory mask of FIG. 1 and illustrates the forehead pad in cross-section.

Referring now to FIG. 7, the forehead support 8A and forehead pad 12A may be embodied as co-moulded components. The forehead pad 12A is formed by injection-moulding an elastomeric material onto the forehead support 8A which is made from a dimensionally stable plastic material, such as a polycarbonate. A slot 44A is formed in the forehead pad 12A during the overmoulding process by virtue of the shape of the forehead support 8A. The slot 44A provides a mechanical interlock such that the forehead support 8A can be releasably secured to the forehead support 8A. There is no intended or significant adhesive bond between the forehead support 8A and forehead pad 12A in this embodiment. This may be achieved by not using a surface pre-treatment and/or overmoulding the parts once the forehead support 8A is completely set (i.e. after moulding). The benefit of not including a substantive bond in this instance is that the forehead support can be removed for separate cleaning or replaced with a new or different type of forehead support.

Advantageously, overmoulding the forehead pad 12A to the forehead support 8A eliminates the assembly step of mounting the forehead pad 12A to the forehead support 8A, reducing the cost of goods and increasing convenience to the patient.

5.4 Flexible Portion

Figure 8:
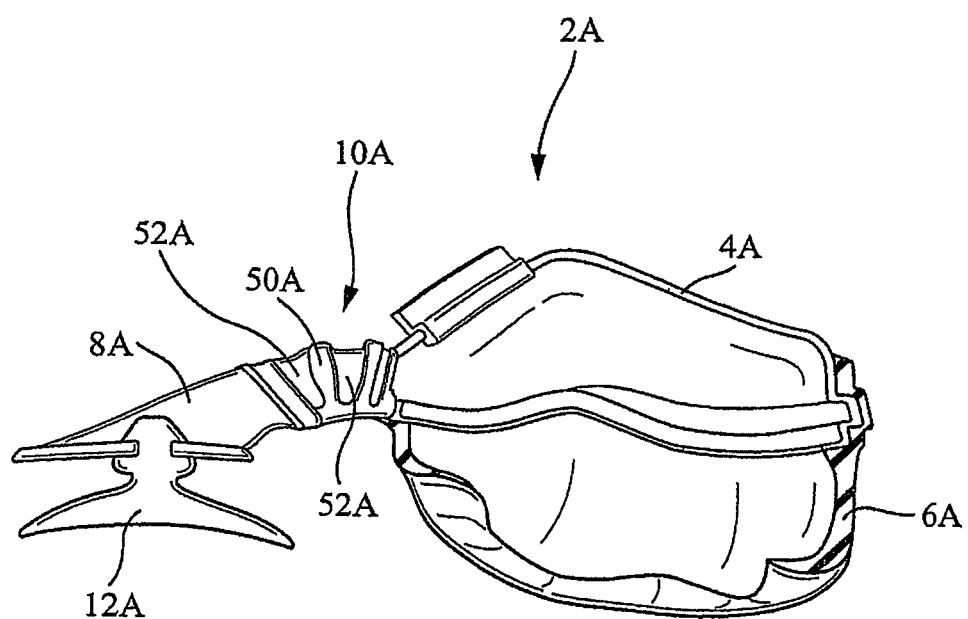
FIG. 8 is a side, partial cross-sectional view of the respiratory mask of FIG. 1 and illustrates a flexible portion between the frame and forehead support according to an embodiment of the present invention.

The flexible portion 10A will now be described with reference to FIG. 8. The flexible portion 10A comprises a structural spine 50A and a number of elastomer discs 52A that have been co-moulded onto the spine 50A and between the frame 4A and the spine 50A. Because the elastomer discs 52A are flexible, the frame 4A is able to articulate with respect to the forehead support 8A. The elastomer discs 52A may be made from the same elastomer material that the cushion 6A is made out of or from a different flexible material. In an alternative embodiment the elastomer discs 52A comprise bladders formed from an elastomeric material (or otherwise) that are filled with a compressed gas, liquid or soft solid such as foam, gel or mineral particles.

Figure 9:
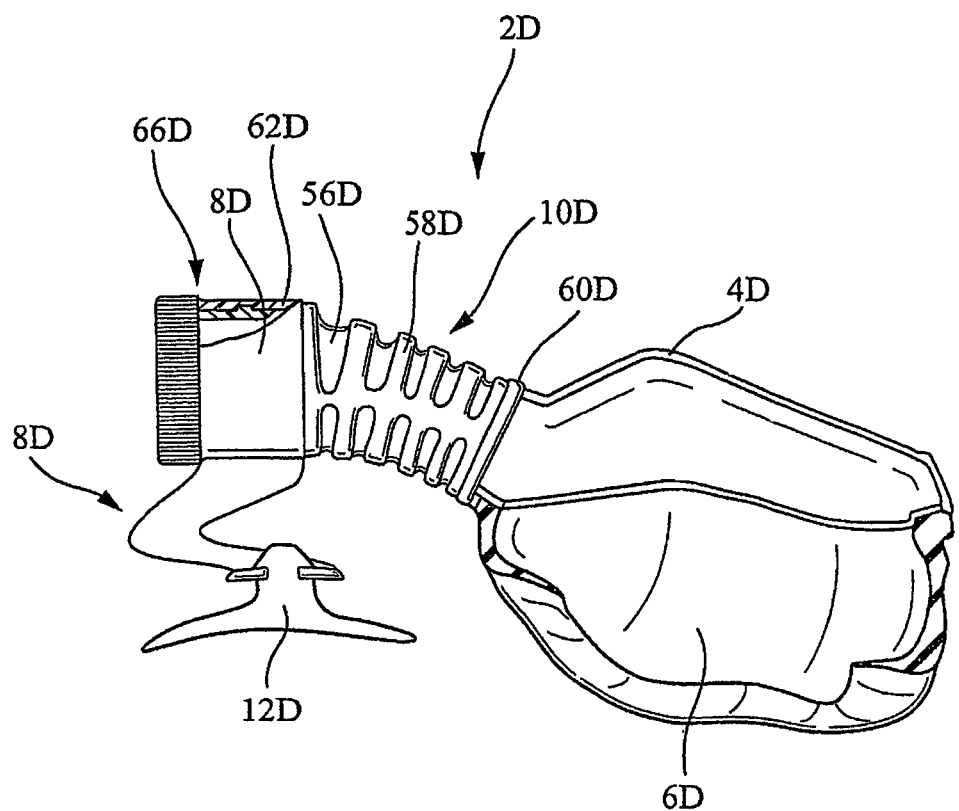
FIG. 9 is a side, partial cross-sectional view of a respiratory mask according to a fourth embodiment of the present invention and illustrates a flexible portion that incorporates a conduit section therethrough.

FIG. 9 shows another embodiment of a mask 2D having a flexible portion 10D including an elastomer tube 56D around which a less flexible exoskeleton 58D is disposed. The ends 60D & 62D of the elastomer tube 56D have been comoulded to the frame 4D and forehead support 8D, respectively. This arrangement allows the frame 4D to articulate with respect to the forehead support 8D, and consequently, the cushion 6D to rotate and move to a degree with respect to the patient's face. This means that the mask 2D is able to provide a better seal against the patient's face. This elastic deformation behavior can be varied by changing the wall thickness or wall section of the exoskeleton 58D.

The elastomer tube 56D may be made from the same elastomer material that the cushion 6D is made out of or from a different flexible and co-mouldable material.

In this case, the elastomer tube 56D provides a fluid passageway that extends between an inner region of the frame 4D and the forehead support 8D where the fluid passageway terminates in a connection 66D. The connection 66D is adapted for receiving one end of a conduit (not shown) that is in fluid communication with an outlet port of a flow generator (not shown).

A mask in accordance with other embodiments of this invention may include a translatable adjustment rather than a rotatable adjustment.

5.5 Elbow & Frame Socket

Figure 10:
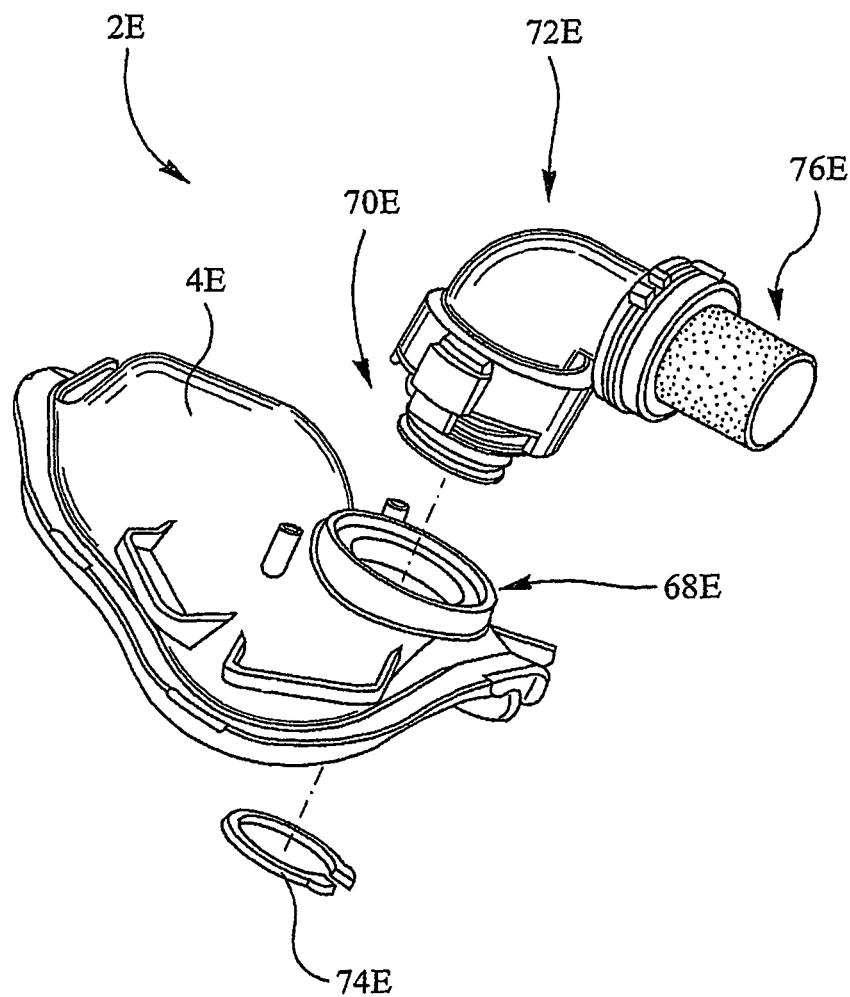
FIG. 10 is a perspective exploded view of a respiratory mask frame, elbow and elbow retaining clip according to a fifth embodiment of the present invention illustrating a bonded elastomer sealing portion on the elbow.

Referring to FIG. 10, a mask 2E is shown which has a frame 4E that comprises a socket 68E that is adapted to receive a first end 70E of an elbow 72E. The first end 70E of the elbow 72E is swivel mounted to the socket 68E and the elbow 72E provides fluid communication between a conduit (not shown) and the mask 2E. A clip 74E is provided to the first end 70E of the elbow 72E to retain it in the socket 68E in use.

In FIG. 10 the second end 76E of the elbow 72E has an elastomer portion 76E co-moulded thereto to provide an improved connection and seal with the conduit to which it is attached. In an alternative embodiment (not shown), the conduit has an elastomer sealing portion rather than the second end 76E.

Figure 11:
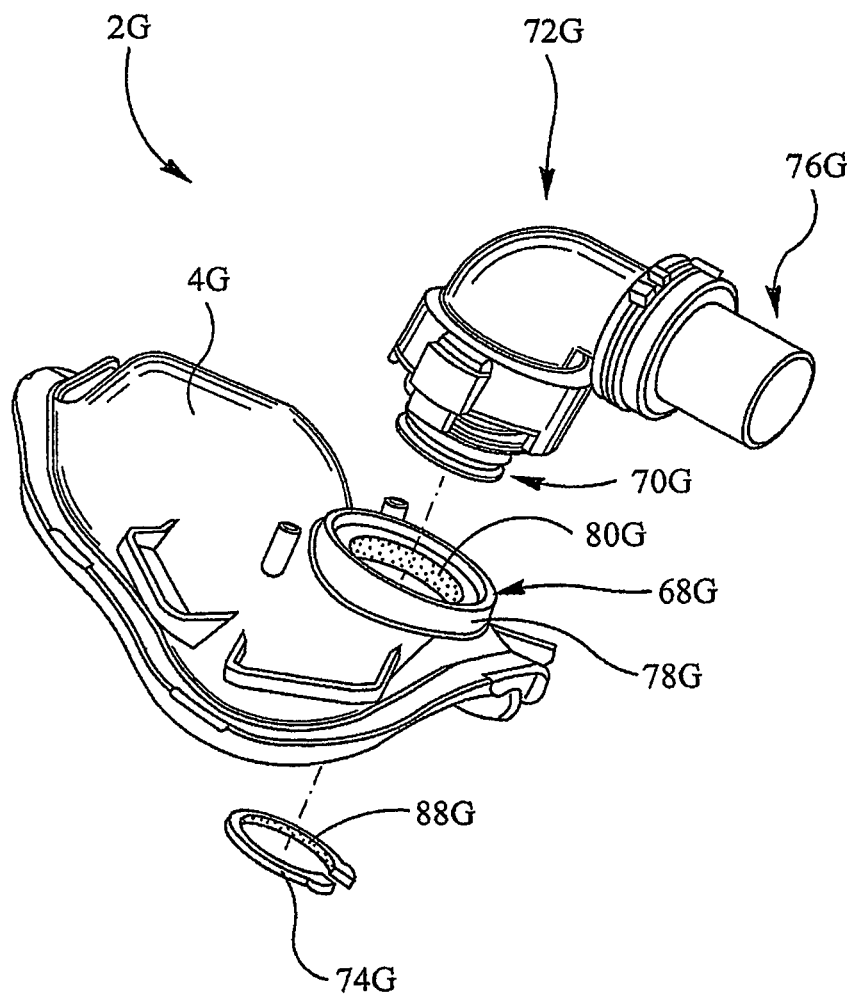
FIG. 11 is a perspective exploded view of a respiratory mask frame, elbow and elbow retaining clip according to a sixth embodiment of the present invention illustrating a number of additional bonded elastomer sealing portions on the socket and retaining clip.

Referring to FIG. 11 the socket 68G has a dimensionally rigid material portion 78G and an elastomer portion 80G co-moulded onto an inner surface thereof. The elastomer portion 80G provides a better seal with the first end 70G of the elbow 72G in use. The clip 74G also includes an elastomer portion 88G co-moulded thereon. This provides a more acoustically pleasing clipping sound.

Figure 12:
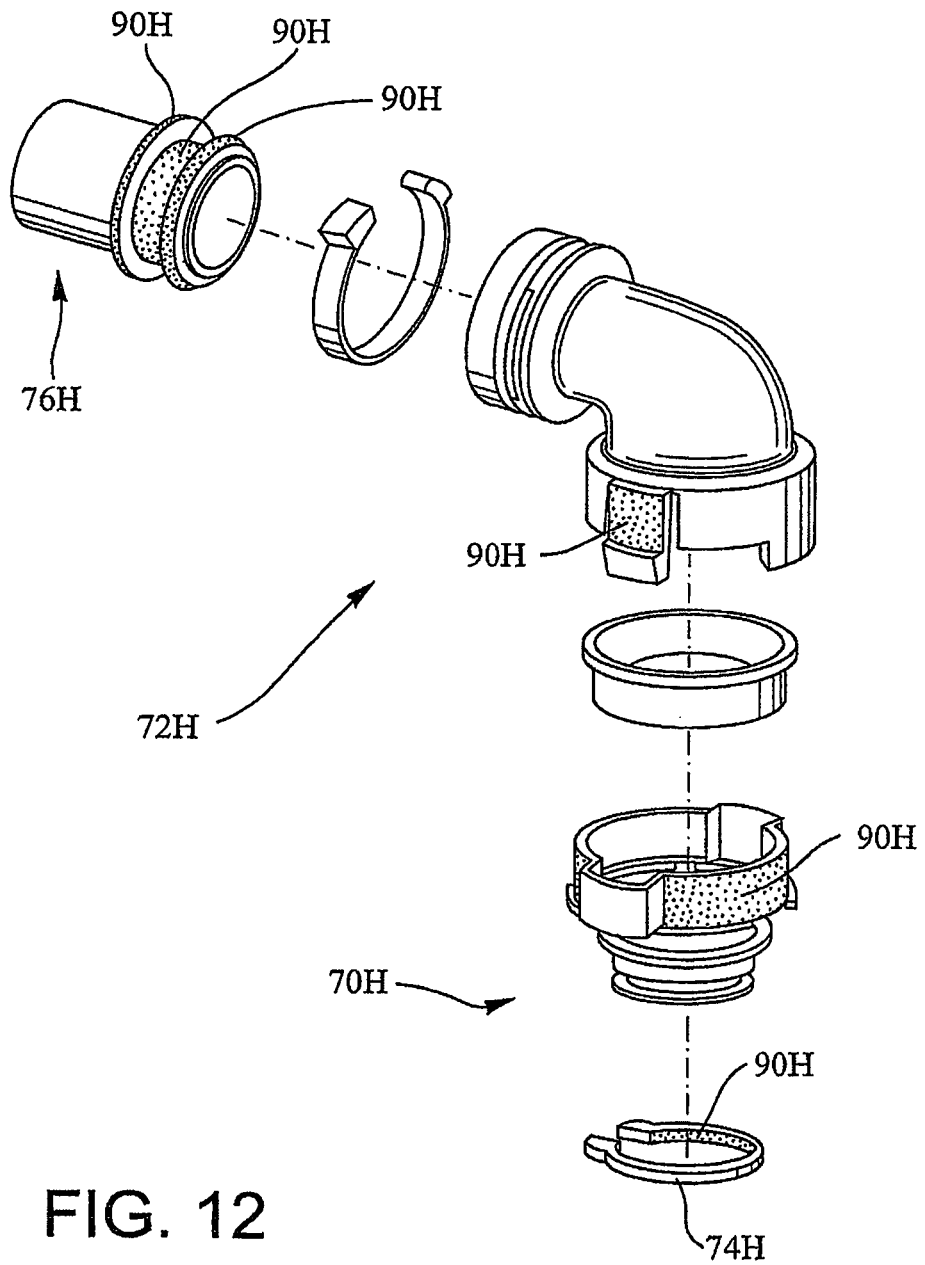
FIG. 12 is a perspective exploded view of an elbow of a respiratory mask according to a seventh embodiment of the present invention illustrating a number of bonded elastomer sealing portions.
Figure 16:
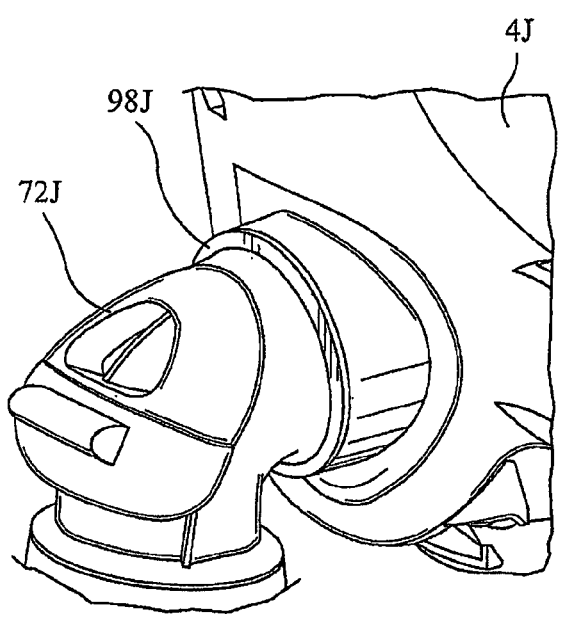
FIG. 16 is a perspective view of a portion of a respiratory mask frame and elbow according to a ninth embodiment of the present invention.
Figure 17:
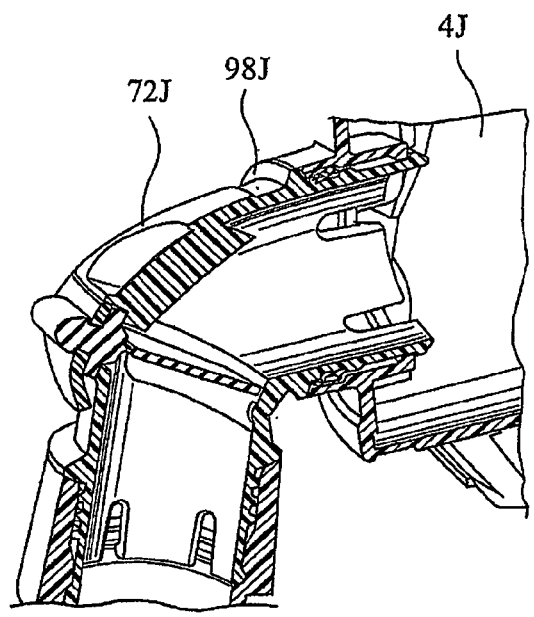
FIG. 17 is a perspective, cross-sectional view of the portion of the frame and elbow of FIG. 16.
Figure 18:
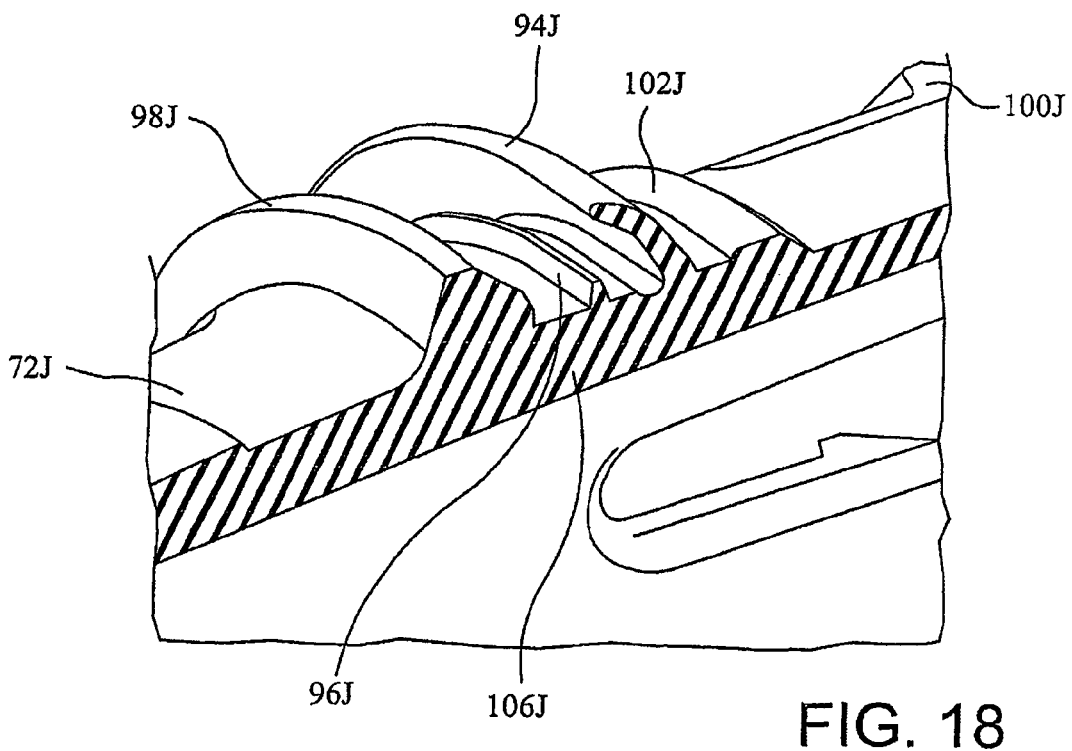
FIG. 18 is an enlarged, perspective, cross-sectional view of the elbow of FIG. 16 illustrating the elbow sealing arrangement.
Figure 19:
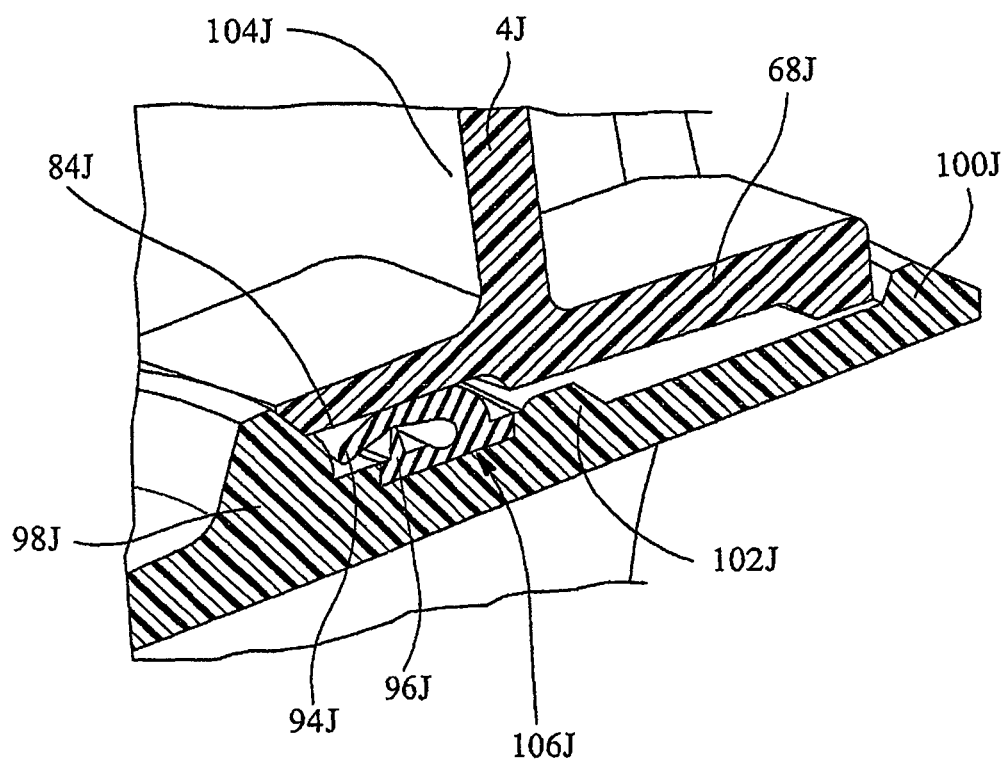
FIG. 19 is a perspective, cross-sectional view of a portion of the respiratory mask frame and elbow of FIG. 16.

FIG. 12 illustrates an elbow 72H generally similar in design and construction to the elbow of FIGS. 10 & 11 in its component parts. The elbow 72H features a number of elastomer portions 90H that serve to aid sealing, dampening, the reduction of rattle and/or the tactility and acoustics of connecting parts.

A number of different elbow-to-frame sealing arrangements will now be described. These are suitable for use on a variety of masks. Following this a sealing elbow arrangement for the ResMed Meridian mask [U.S. Provisional Patent Application No. 60/682,827] and a sealing arrangement for the ResMed Swifi mask [U.S. Provisional Patent Application No. 60/734,282] will be described, each incorporated by reference in its entirety.

5.5.1 Two Stage Radial Elbow to Frame Seal A

FIGS. 13 to 15 show a two stage radial seal 92I comoulded to an elbow 72I and adapted to seal against a frame 4I. The seal 92I comprises a long elastomer lip 94I that abuts an inner surface 84I of a socket 68I of a frame 4I. The seal 92I further comprises two shorter lips 96I that are moulded in the line of draw. In use, the long lip 94I presses into the socket 68I and flexes back onto the two shorter lips 96I such that the long lip 94I is supported in a position where it abuts and seals against the socket 68I. This geometry accommodates misalignment of the elbow 72I with respect to the frame 4I.

The elbow 72I further incorporates three circumferential flanges. A first flange 98I is integrally moulded to the elbow 72I to prevent the seal 92I from contacting any flat supporting surface when the elbow 72I is disassembled from the frame 4I. This minimises risk of damage to the seal 92I during transport, storage and cleaning. A second flange 100I is provided on the elbow 72I and engages the socket 68I to stabilize the elbow 68I. While in this embodiment the second flange 100I is located inboard from the seal 92I, in other embodiments it could be moved outboard providing a greater moment arm. A third flange 102I is positioned within the socket 68I to engage a shoulder 103I of the elbow 4I, adjacent where the socket 68I begins to extend beyond the outer surface 104I of the frame 4I.

Another embodiment (not shown) is also provided where only a line contact seal is provided to the frame 4I as opposed to an area contact seal. A line contact seal reduces the torque required to rotate the elbow with respect to the frame.

It should also be noted that this design avoids undercuts and crevices to ensure ease of cleaning.

FIG. 13 also depicts an anti-asphyxia valve having a base portion 103I that is co-moulded to an elbow clip 105I of the elbow 72I. This overmoulding step replaces an assembly step reducing the cost of goods and increasing convenience to the patient.

5.5.2 Two Stage Radial Elbow to Frame Seal B

The embodiment shown in FIGS. 16 to 19 includes a seal 106J that is similar to the seal 92I of FIGS. 13-15 except that the seal geometry has been altered to provide less contact area between the seal 106J and the frame 4J. The seal 106J comprises a long elastomer lip 94J and one shorter lip 96J that are moulded in the line of draw. The long lip 94J presses into the socket 68J of the frame 4J and flexes back onto the shorter lip 96J such that the long lip 94J is supported in a position abutting and sealing with the inner surface 84J of the socket 68J. This geometry accommodates misalignment of the elbow 72J with respect to the frame 4J.

The elbow 72J incorporates three circumferential flanges to stabilize the elbow 72J within the socket 68J. A first flange 98J is positioned outside the socket 68J and frame 4J. The first flange 98J prevents the seal 106J from contacting any flat surface when the elbow 72J is disassembled from the frame 4J thereby reducing the risk of damage to the seal 106J during transport, storage and cleaning. A second flange 100J is positioned outside the socket 68J and inside the frame 4J and abuts the socket 68J to stabilize the elbow 68J. A third flange 102J is positioned within the socket 68J adjacent where the socket 68J begins to extend beyond the outer surface 104J of the frame 4J.

Another embodiment (not shown) is also provided where only a line contact seal is provided to the frame 4J as opposed to an area contact seal. A line contact seal reduces the torque required to rotate the elbow with respect to the frame.

This design avoids undercuts and crevices to ensure ease of cleaning.

5.5.3 Single Radial Seal

Referring to the mask 2K of FIGS. 20-22 an elbow 72K is provided having a single radial lip seal 108K that acts on an inner surface 84K of a socket 68K. The elbow 72K incorporates four circumferential flanges to support and stabilize the elbow 72K on the frame 4K. A first flange 98K is positioned outside the socket 68K and frame 4K. A second flange 100K is positioned outside the socket 68K and inside the frame 4K. A third and fourth flange, 102K & 110K respectively, are positioned on either side of the seal 108K. This design avoids undercuts and crevices to ensure ease of cleaning.

5.5.4 Double Radial Seal

Figures 23, 24:
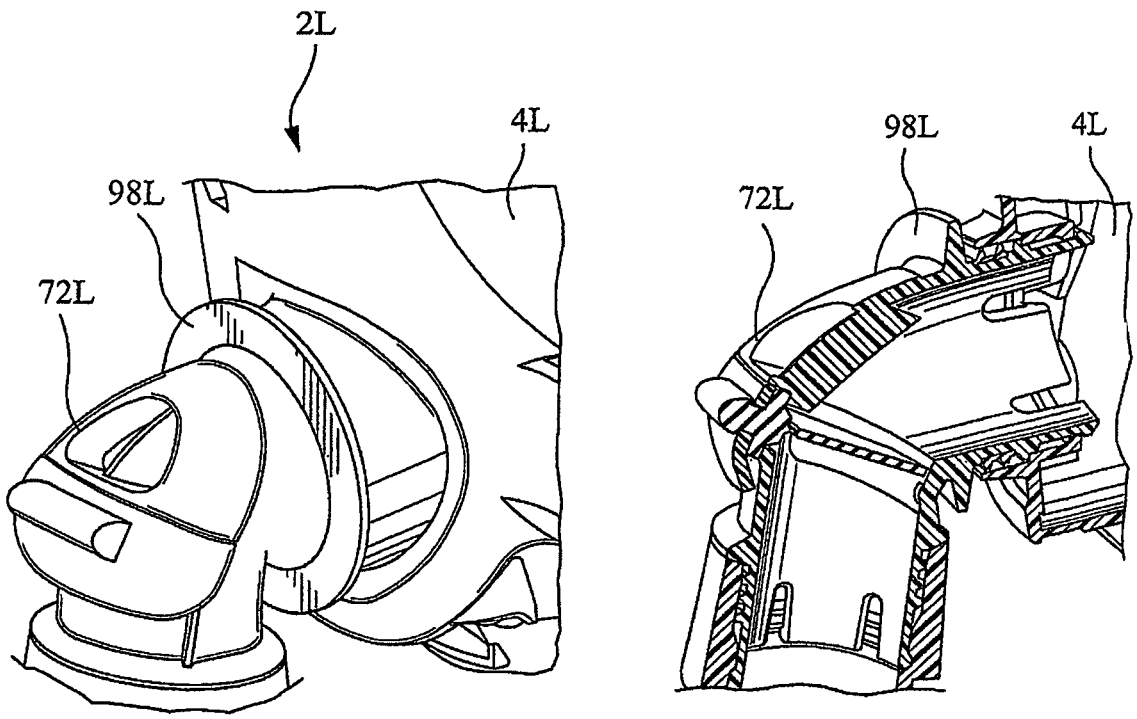
FIG. 23 is a perspective view of a portion of a respiratory mask frame and elbow according to a eleventh embodiment of the present invention.
FIG. 24 is a perspective, cross-sectional view of the portion of the frame and elbow of FIG. 23.
Figure 25:
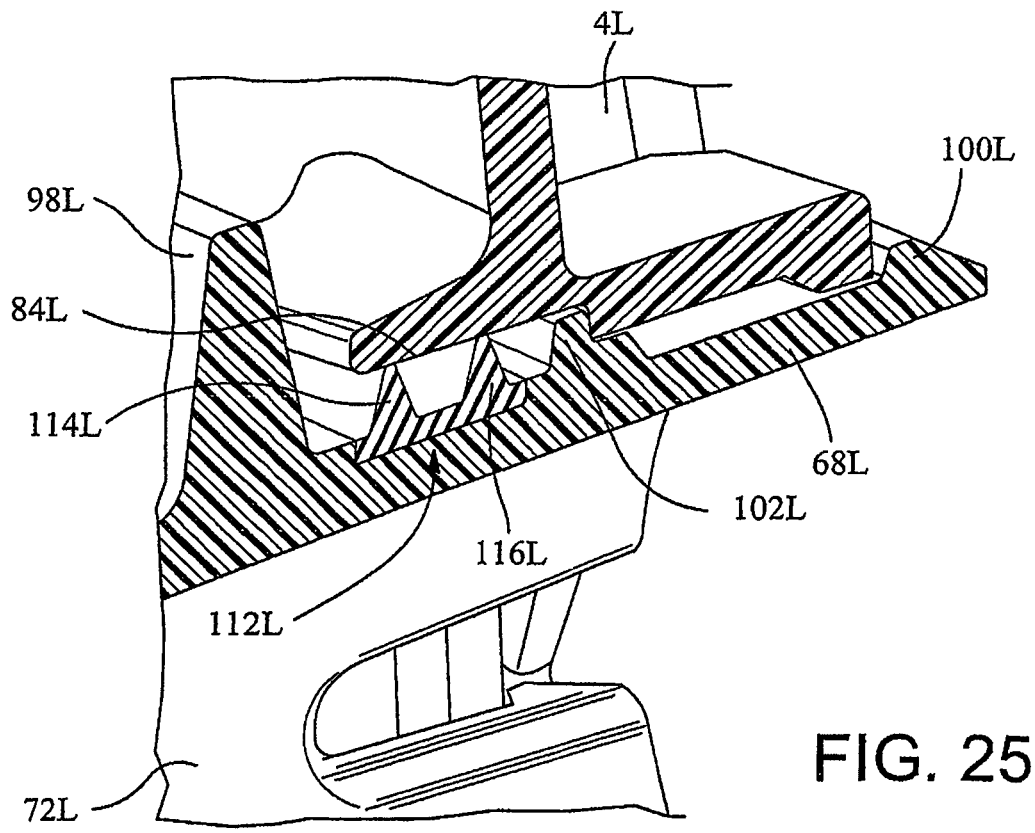
FIG. 25 is an enlarged, perspective, cross-sectional view of the frame and elbow of FIG. 23 illustrating the elbow sealing arrangement.

FIGS. 23 to 25 show a mask 2L incorporating a double radial seal 112L. The double radial seal 112L has two lips 114L & 116L, respectively, adjacent each other, that seal against an inner surface 84L of a socket 68L of a frame 4L. Each lip 14L, 116L is configured with a generally triangular cross-section such that it has a degree of stiffness to enhance sealing.

The elbow 72L incorporates three circumferential flanges 98L, 100L & 102L that are arranged in the same fashion as the embodiment of Section 5.5.1 and FIGS. 13-15. This design avoids undercuts and crevices to ensure ease of cleaning.

5.5.5 External Seal

Figure 26:
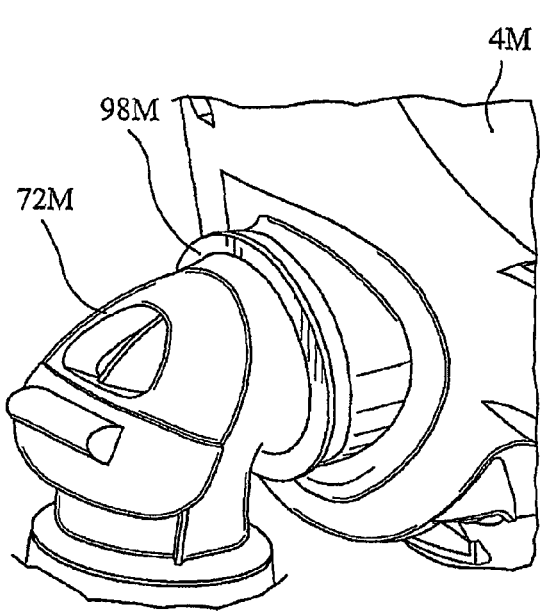
FIG. 26 is a perspective view of a portion of a respiratory mask frame and elbow according to a twelfth embodiment of the present invention.
Figure 27:
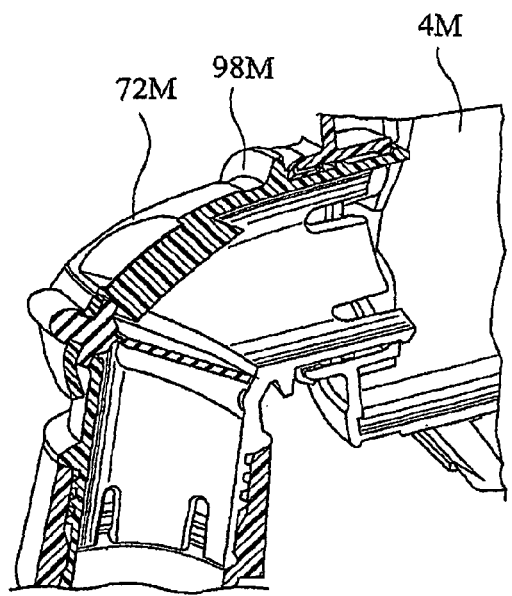
FIG. 27 is a perspective, cross-sectional view of the portion of the frame and elbow of FIG. 26.
Figure 28:
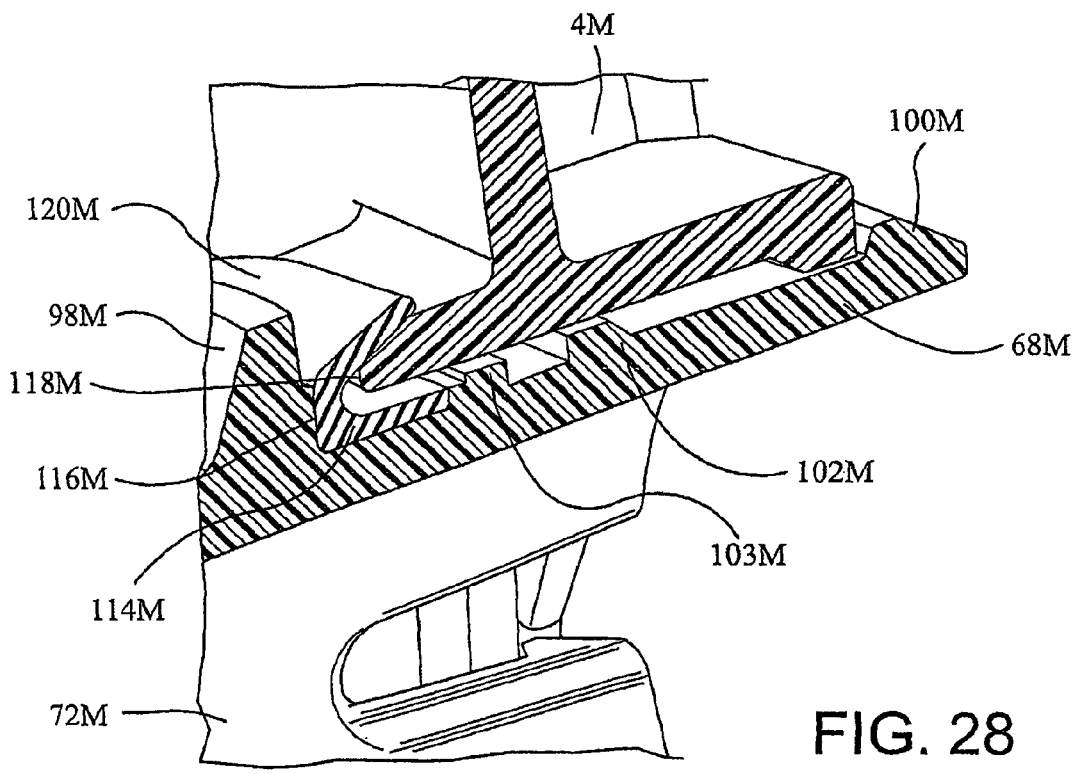
FIG. 28 is an enlarged, perspective, cross-sectional view of the frame and elbow of FIG. 26 illustrating the elbow sealing arrangement.

The embodiment shown in FIGS. 26-28 provides 3 sealing zones between the elbow 72M and the socket 68M. The 3 sealing zones include a radial seal 114M disposed on the elbow 72M inside the socket 68M, an axial seal 116M that seals against an end face 118M of the socket 68M and an external radial lip seal 120M that seals against an outside the socket 68M.

The elbow 72M incorporates four circumferential flanges 98M, 100M, 102M and 103M to stabilize and support the elbow 72M within the socket 68M. Additionally, the first flange 98M of the circumferential flanges is sized and adapted to prevent the seal 120M from contacting any flat supporting surface when the elbow 72M is disassembled from the frame 4M. This minimises risk of damage to the seal 120M during transport, storage and cleaning.

5.5.6 Radial & Axial Seal Combination

Figure 29:
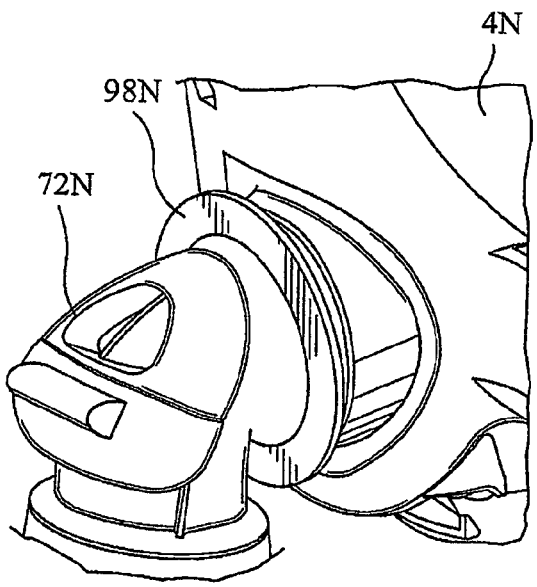
FIG. 29 is a perspective view of a portion of a respiratory mask frame and elbow according to an thirteenth embodiment of the present invention.
Figure 30:
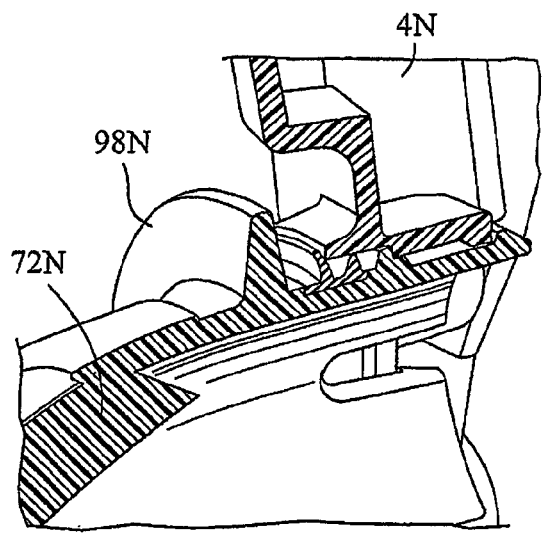
FIG. 30 is a perspective, cross-sectional view of the portion of the frame and elbow of FIG. 29.
Figure 31:
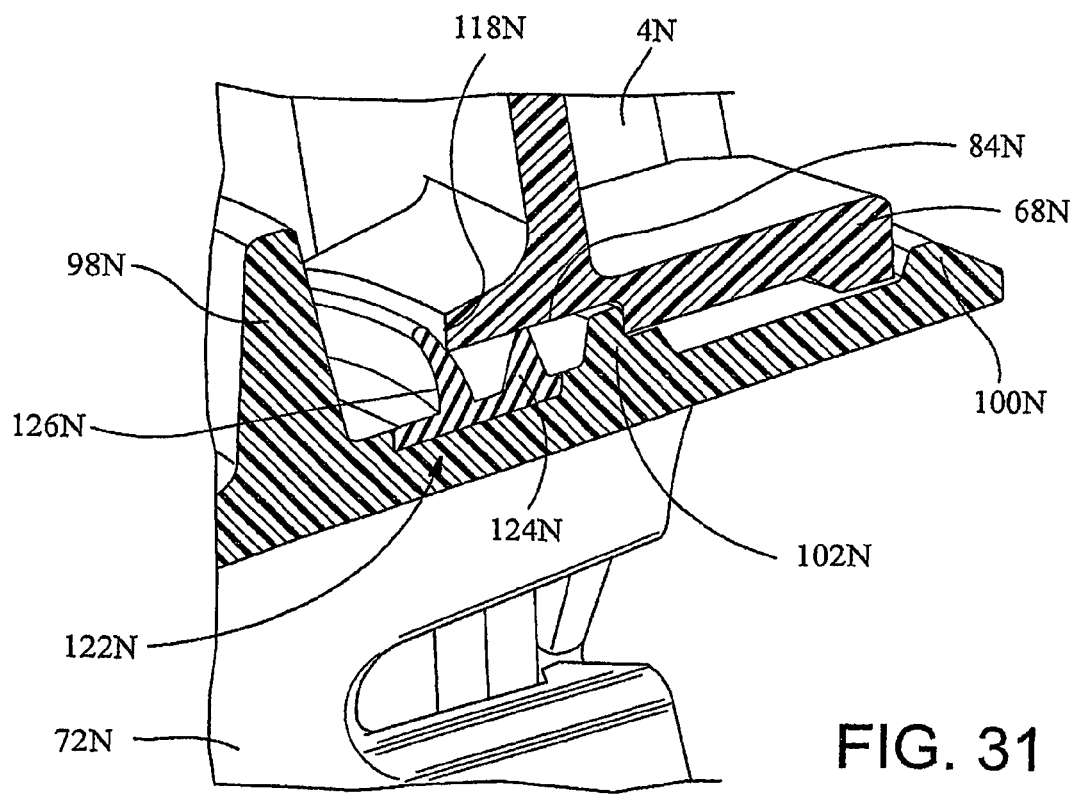
FIG. 31 is an enlarged, perspective, cross-sectional view of the frame and elbow of FIG. 29 illustrating the elbow sealing arrangement.

Referring to FIGS. 29-31 a sealing arrangement 122N is shown. The sealing arrangement 122N comprises a radial lip seal 124N of triangular cross-section that seals against an inner surface 84N of the socket 68N and an axial lip seal 126N that seals against an end face 118N of the socket 68N.

The elbow incorporates the same arrangement of three circumferential flanges for stabilization of the elbow 72N within the socket 68N as is provided in the embodiment of FIGS. 13-15 described in Section 5.5.1.

5.5.7 ResMed Meridian Mask [U.S. Patent Application No. 60/682,827]

Figure 32:
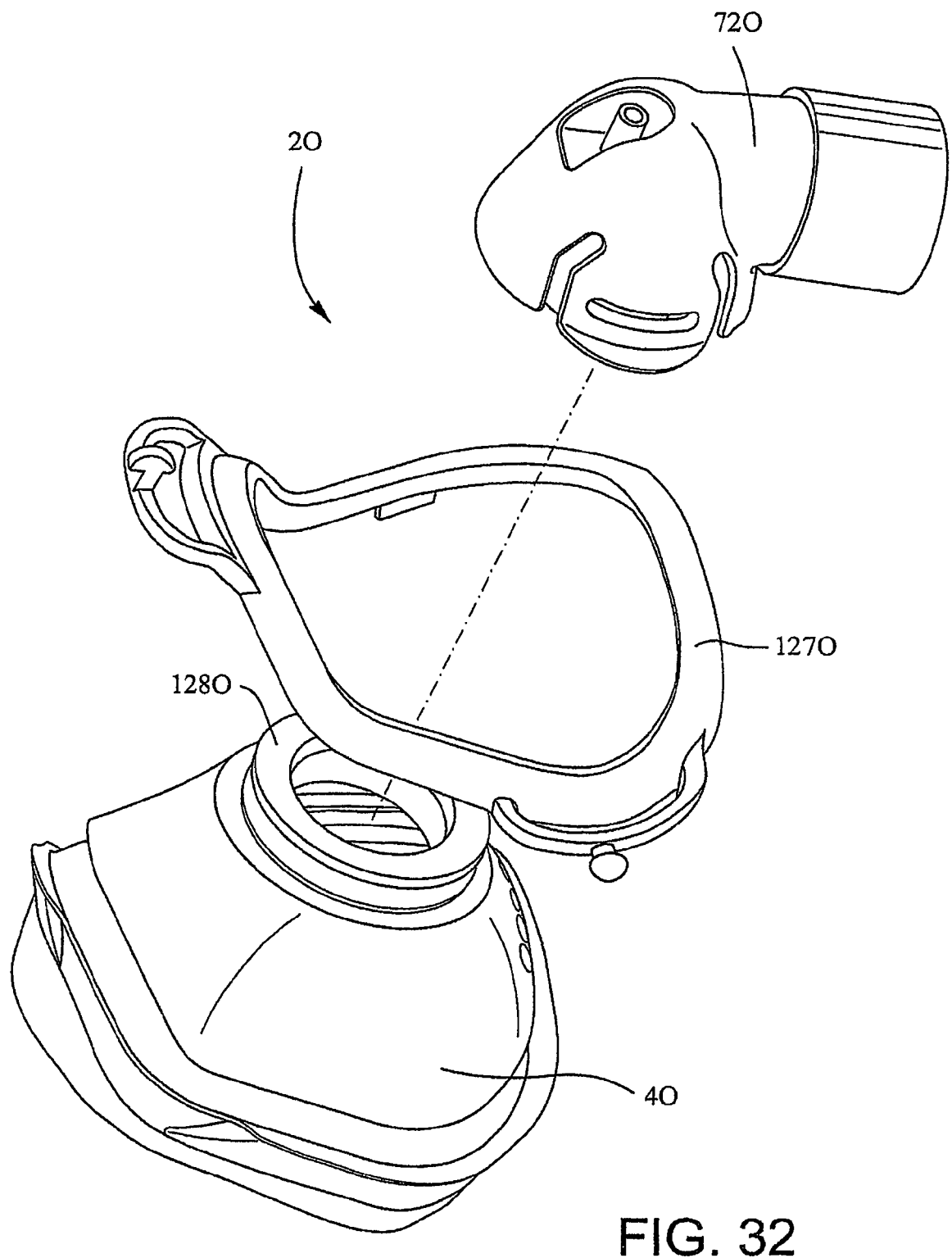
FIG. 32 is a perspective, exploded view of an elbow and a frame having a flexible enclosure, a rigid elbow connection ring defining an aperture in the frame and a rigid surrounding portion according to a fourteenth embodiment of the present invention.

The contents of U.S. Patent Application No. 60/682,827 are incorporated herein by reference in their entirety. Referring to FIG. 32, the ResMed Meridian Mask Assembly 2O comprises a flexible silicone frame 4O having a hard peripheral portion 127O, a polycarbonate elbow 72O and a retaining ring 128O that is used to connect the frame 4O to the elbow 72O and allow them to swivel relative to each other.

The elastomer frame 4O can be overmoulded to the retaining ring 128O. This ameliorates any difficulties encountered in mounting the ring 128O on the frame 4O and takes away the step of connecting the two parts during assembly.

5.5.8 ResMed Swift Mask Elbow [U.S. Patent Application No. 60/758,200]

Figure 33:
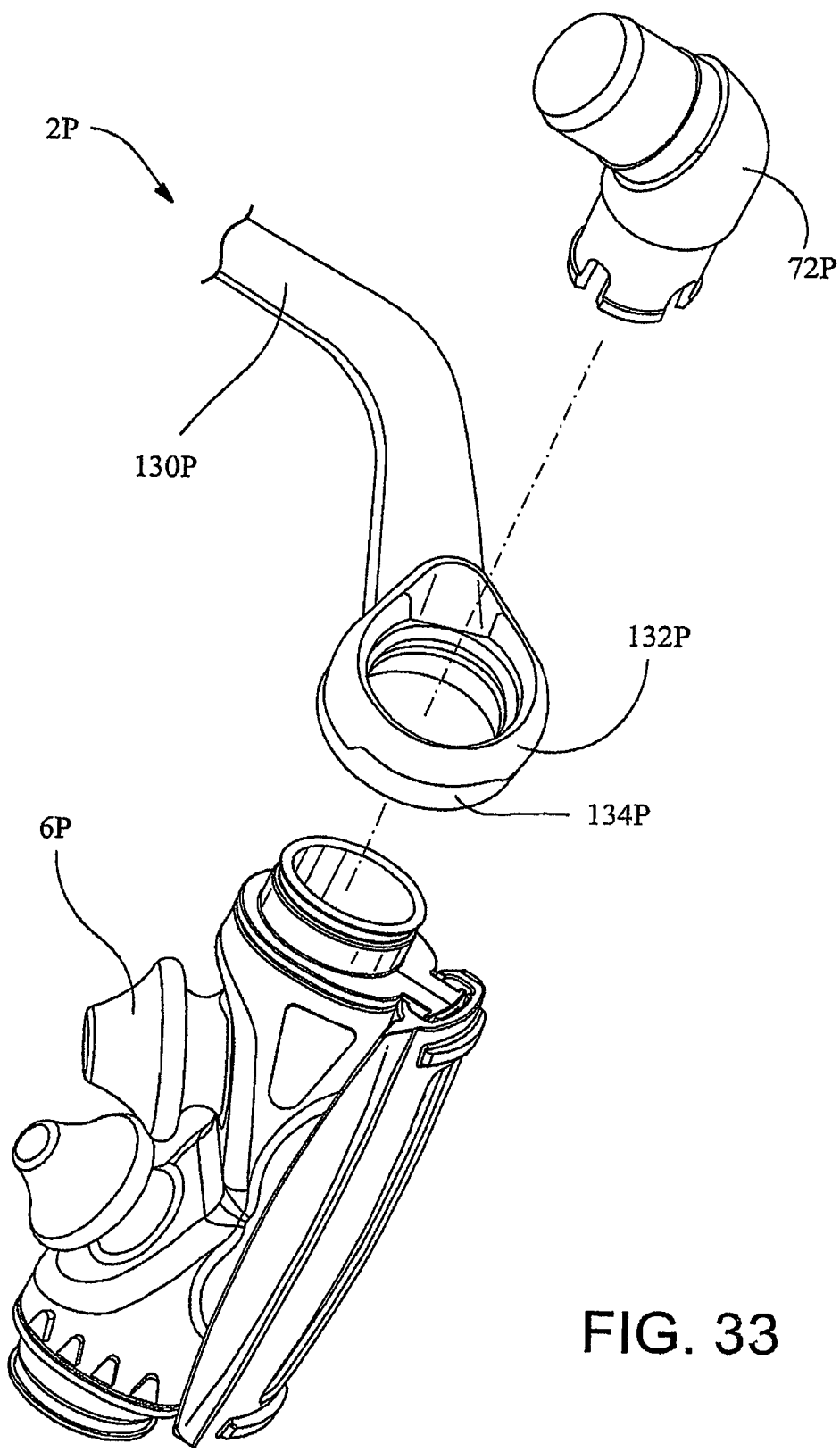
FIG. 33 is a perspective, exploded view of an elbow, frame and headgear member according to a fifteenth embodiment of the present invention.

The contents of U.S. Patent Application No. 60/758,200, filed Jan. 12, 2006 are incorporated herein by reference in their entirety. Referring to FIG. 33, a portion of a ResMed Swift Mask 2P is shown including a cushion assembly 6P, yoke 130P that is attached to a headgear strap, seal 132P and elbow 72P. The yoke 130P includes a yoke ring 134P that is adapted to surround a portion of the seal 132P and the seal 132P is adapted to surround a portion of the elbow 72P. The cushion assembly 6P may be adjustably rotated with respect to the yoke 130P.

Seal 132P may be overmoulded to the yoke ring 134P. This ameliorates difficulties sometimes encountered in mounting the seal 132P on the yoke ring 134P and takes away the step of connecting the two parts during assembly.

5.6 Gas Washout Device

Figure 34:
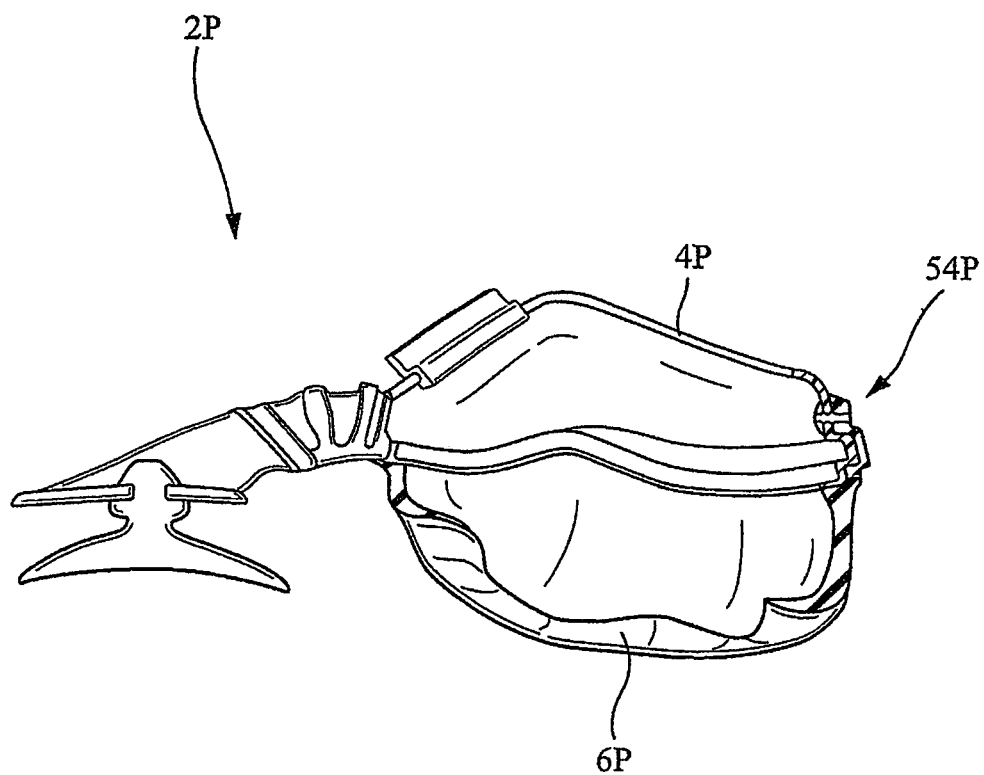
FIG. 34 is a side, partial cross-sectional view of a respiratory mask according to a sixteenth embodiment of the present invention and illustrates a vent.

Referring to FIG. 34, the frame 4P includes a co-moulded vent 54P for allowing exhaled breath to exit an interior region of the frame 4P into the surrounding environment. The vent 54P is formed from an elastomer material that has been co-moulded to the frame 4P. The geometry of the frame 4P and vent 54P are such that they mechanically engage in a manner that allows the vent 54P to be retained or removed from the frame 4P, as required.

In another embodiment, the vent 54P is substantially inseparably coupled to the frame 4P by a chemical bond in addition to the mechanical interlock. The vent may also be embodied as an insert that comprises a plurality of fluid conduits (or vent holes or pores (e.g., sintering)) that connect the interior region of the frame 4P to the surrounding environment.

5.6.1 Sealing a Vented Mask to Make a Non-Vented Mask

Figure 35:
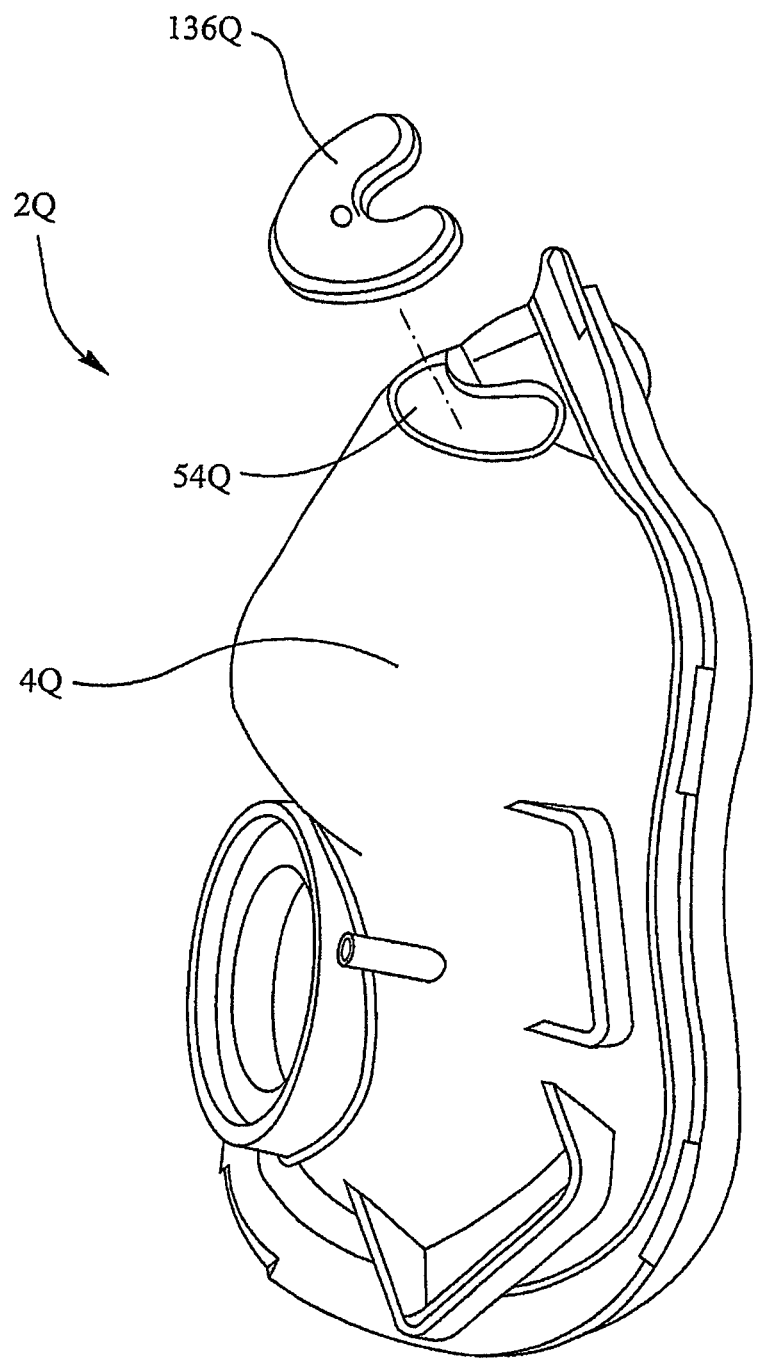
FIG. 35 is a perspective exploded view of a respiratory mask frame and vent plug according to a seventeenth embodiment of the present invention.
Figure 36A:
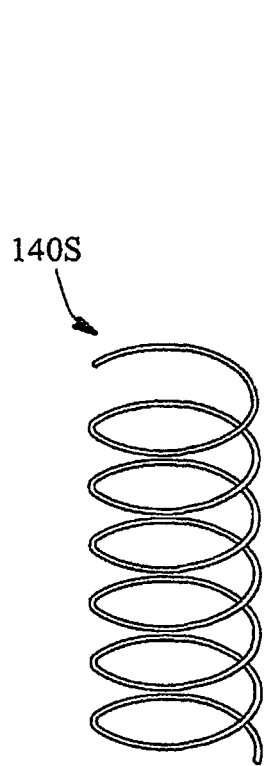
FIGS. 36(a)-36(d) are schematic diagrams showing three types of conduit reinforcing structure according to eighteenth, nineteenth, twentieth and twenty first embodiments of the present invention, respectively.
Figure 36B:
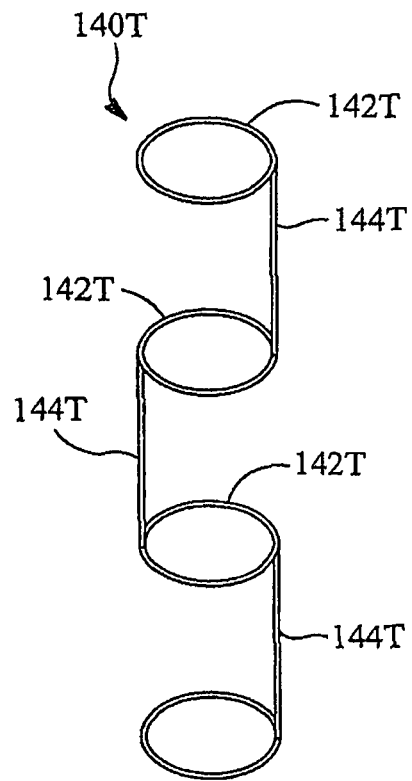
Figure 36C:
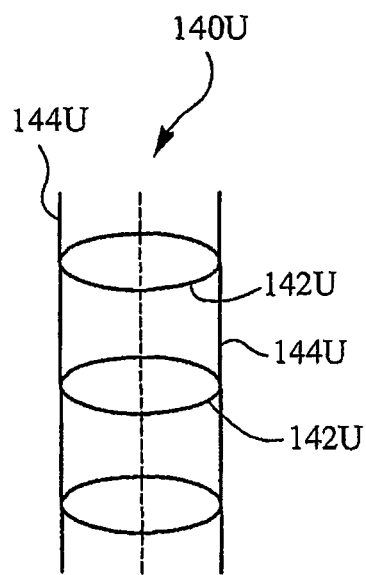
Figure 36D:
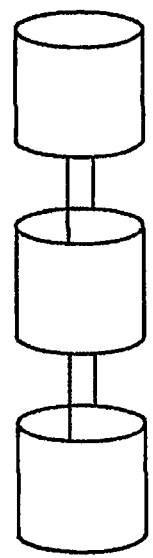

FIG. 35 depicts a vented mask 2Q having a vent aperture 54Q and a plug 136Q. For ease of visualization FIG. 35 shows the plug 136Q separately from the mask 2Q but in reality the plug 136Q is formed in the vent 54Q by overmoulding to form a non-vented mask. In this case, the plug 136Q is formed from silicone.

This process means that a single mask frame 4Q is a suitable component for either a vented or a non-vented mask. This reduces manufacturing costs because only one frame 4Q needs to be moulded for both types of mask.

In the case that non-vented therapy is being delivered to a patient, the plug 136Q is permanently attached to the frame 4Q. Advantageously, this avoids user interference with the equipment (e.g. removal of the plug 136Q) and subsequent therapy problems. This permanent attachment may be achieved through the aforementioned plasma pre-treatment. Alternatively, the plug 136Q may be temporarily attached, and in this case the mask 2Q could be used to provide either vented or non-vented therapy.

5.7 Conduit

Methods of conduit manufacture utilizing overmoulding will now be described. The fundamental technical issues addressed by the overmoulding technique in the context of conduits is the development of a conduit which is both flexible yet does not occlude in use. Overmoulding allows a flexible membrane conduit wall to be attached or bonded to a less flexible conduit structure, the purpose of which is to prevent occlusion of the flexible wall.

In one embodiment, the conduit structure is configured as a reinforcement structure, e.g., an exoskeleton over/within, and/or inside the flexible conduit wall. Clearly, where the conduit structure extends continuously along the conduit wall, the conduit structure must be formed of a flexible material to allow the conduit to bend. Fastening of the flexible wall to the conduit structure may be achieved by either mechanical engagement, molecular bonding or both.

Three embodiments of conduit structures are shown in FIGS. 36(*a*)-36(*c*). The first, shown in FIG. 36(*a*), is a helical conduit structure 140S that provides significant torsional strength. The second conduit structure 140T, shown in FIG. 36(*b*), comprises a plurality of circular ribs 142T interconnected by longitudinal members 144T that are provided on alternating opposing sides of the conduit wall (not shown). FIG. 36(*c*) depicts a third conduit structure 140U comprising a plurality of circular ribs 142U interconnected by dual longitudinal members 144U that are provided on opposing sides of the conduit wall (not shown). FIG. 36(*d*) depicts a fourth conduit structure 145.

5.8 Ports Cap

Figure 37:
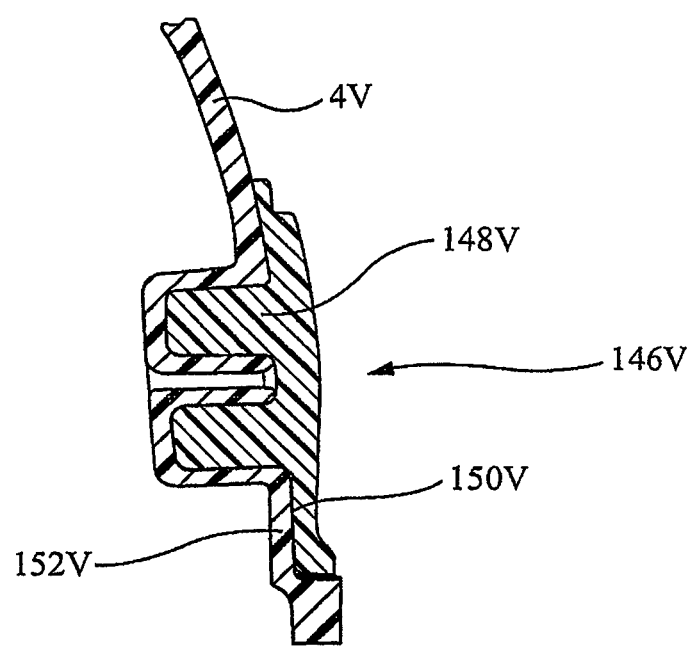
FIG. 37 is a side, cross-sectional view of a ports cap configured on a frame of a respiratory mask according to a twenty-second embodiment of the present invention.

FIG. 37 shows a ports cap 146V co-moulded to the frame 4V. The ports cap 146V comprises a cover portion 148V and a hinge portion 150V that is permanently bonded to an adhesion region 152V of the frame 4V. The cover portion 148V is only lightly or marginally bonded to the frame 4V and can be readily manually separated by a user or clinician the first time the ports cap 146V is used. Advantageously, the ports cap 146V cannot be dropped by a patient or lost. The ports cap 146V can be designed so that it can be reattached to the frame 4V even though the light bond is broken (e.g. by a mechanical interlock such as a rib and groove arrangement).

5.9 Mask Surfaces

5.9.1 Gripping

Manual gripping of mask parts made of hard materials with smooth surfaces (e.g. polycarbonate) can be difficult. This can lead to slippage or movement during manipulation of mask parts. The integration of elastomeric regions onto a mask, and in particular onto a mask frame, assists both manual and robotic gripping. Elastomeric regions may be integrated into a mask solely for this purpose and may provide robots with a controlled grip to handle mask parts for automation, assembly or packaging purposes.

Figure 38:
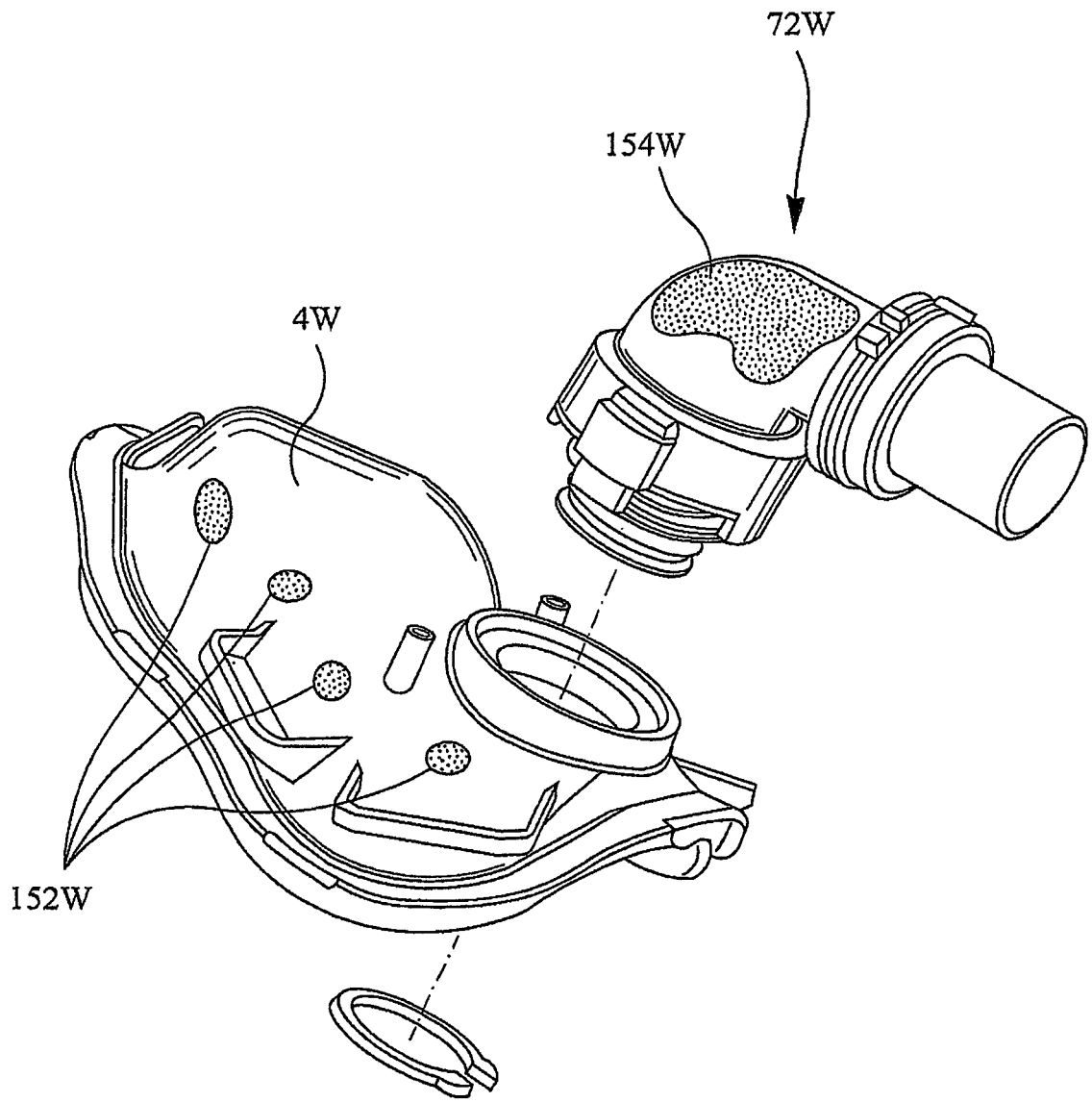
FIG. 38 is a perspective, exploded view of a frame, elbow and elbow retaining clip including a plurality of gripping portions according to a twenty third embodiment of the present invention.

An example of how gripping regions might be incorporated into a mask frame 4W and elbow 72W is illustrated in FIG. 38. A number of small gripping regions 152W are co-moulded onto each side of the frame 4W and at least one relatively large gripping region 154W is co-moulded onto each side of the elbow 72W. The elbow gripping regions 72W assist: (1) gripping of the elbow 72W during manufacture, and/or (2) removal of the elbow 72W from the frame 4W by a patient or clinician.

5.9.2 Soft Touch

Other mask embodiments include one or more soft touch surface(s) co-moulded to the mask frame. The soft touch surface(s) feels nicer and less clinical to a patient than a hard surface(s) (e.g. polycarbonate). By varying the thickness and hardness of a soft touch surface, a range of different feels may be provided. Other parts of respiratory masks may also include soft touch surfaces such as the headgear clips or forehead support.

5.9.3 Branding

Co-moulded elastomer regions also provide suitable surfaces for the placement of product or company branding or logos, e.g., "ResMed" could be spelled out by co-moulding onto various mask components such as the frame, headgear, forehead support, elbow, etc. In one embodiment, the branding indicia is embossed into the elastomer or the elastomer forms the branding indicia. It should be noted that any one elastomer region could be used for a multiplicity of purposes, such as more than one of gripping, soft touch and branding. The elastomer could also be coloured to improve aesthetics, or for branding purposes etc.

5.10 Other Overmoulding Applications for Masks

5.10.1 Mask Volume Reduction Bladder

Figure 39:
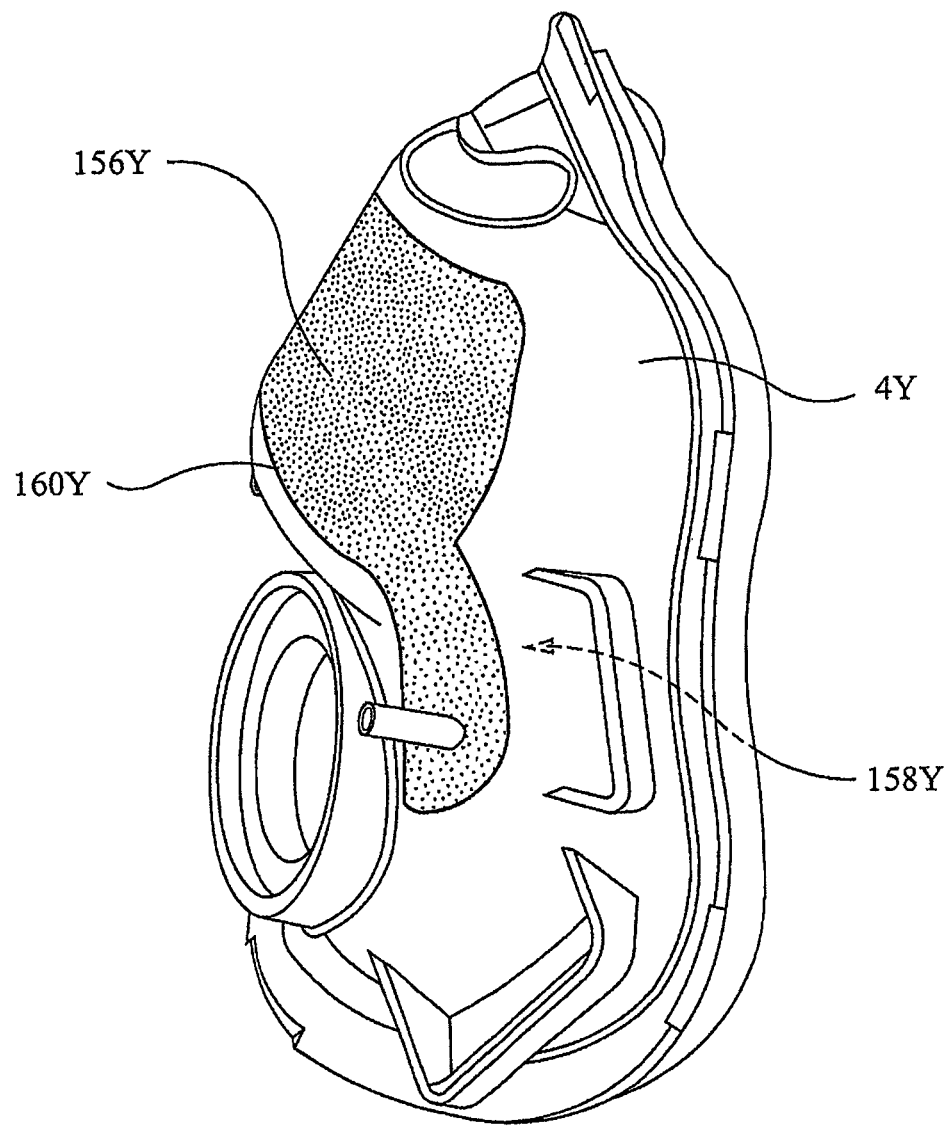
FIG. 39 is a perspective view of a frame including a large gripping portion according to a twenty-fourth embodiment of the present invention.

Referring to FIG. 39, a mask volume reduction bladder (MVRB) 156Y may be incorporated into a mask frame 4Y by overmoulding an expandable pocket onto an interior surface 158Y of the frame 4Y, and more particularly, overmoulding a peripheral edge 160Y of the pocket to the interior surface 158Y of the frame 4Y. The bladder 156Y is positioned and configured such that it is expandable to occupy at least a portion of the gas dead space within the mask. In this particular embodiment, the bladder walls are made from a thin sheet of silicone (0.1-0.6 mm thick).

The bladder may have elastic properties and in an alternative embodiment may be configured within a recess in the frame instead of on an interior surface of the frame. In one variation, the bladder volume is in fluid communication with an interior volume of the frame via a flap valve or other suitable valve. In yet another variation, the frame includes an air passageway between the interior volume of the frame and the interior volume of the bladder.

In another embodiment, the bladder inflates and deflates responsive to the breathing cycle of the patient, reducing the volume required to be displaced by the patient's lungs during exhalation. In yet another embodiment, the bladder deflates during exhalation to increase the volume and thus reduce the expiration pressure peak and subsequently the work of breathing. In another embodiment the bladder is co-moulded to an outer surface of the frame and an interior portion of the bladder is in fluid communication with an inner region of the frame (e.g. via an aperture in the frame). During exhalation the bladder can expand and thus reduce the expiration pressure peak and subsequently the work of breathing.

5.10.2 Removable Oxygen Sensing Cannula

Figure 40:
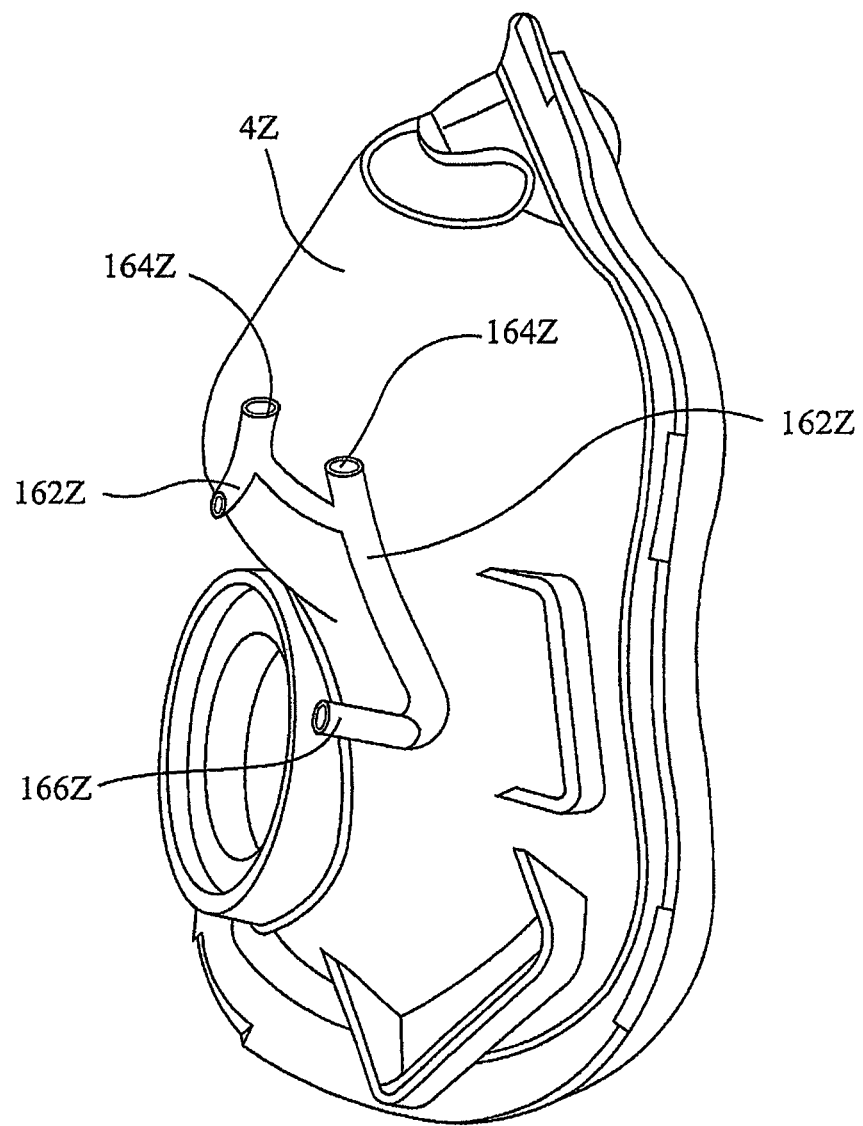
FIG. 40 is a perspective view of a frame including a detachable conduit arrangement according to a twenty-fifth embodiment of the present invention.

FIG. 40 shows a frame 4Z of a respiratory mask incorporating oxygen cannulae 162Z that are formed by overmoulding silicone to an interior surface of the frame 4Z. The cannulae 162Z can be peeled away from the frame 4Z starting at the cannula exit apertures 164Z such that the exit apertures 164Z are positioned directly beneath a patient's nares. The cannulae 162Z are in fluid communication with frame ports 166Z to which an oxygen delivery conduit (not shown) or gas receiving conduit (not shown) may be attached. A gas receiving conduit might be used to receive exhaled breath in order to detect levels of different gases (e.g. oxygen) in the exhaled breath. The frame ports 166Z are sealed by plugs when the cannulae 162Z are not in use and the cannulae 162Z may be completely removed (torn off) the frame 4Z. The plugs may take the same or similar form to those described in Section 5.8.

5.10.3 Humidifier Tub Seal [U.S. patent application Ser. No. 10/533,940]

Figure 41:
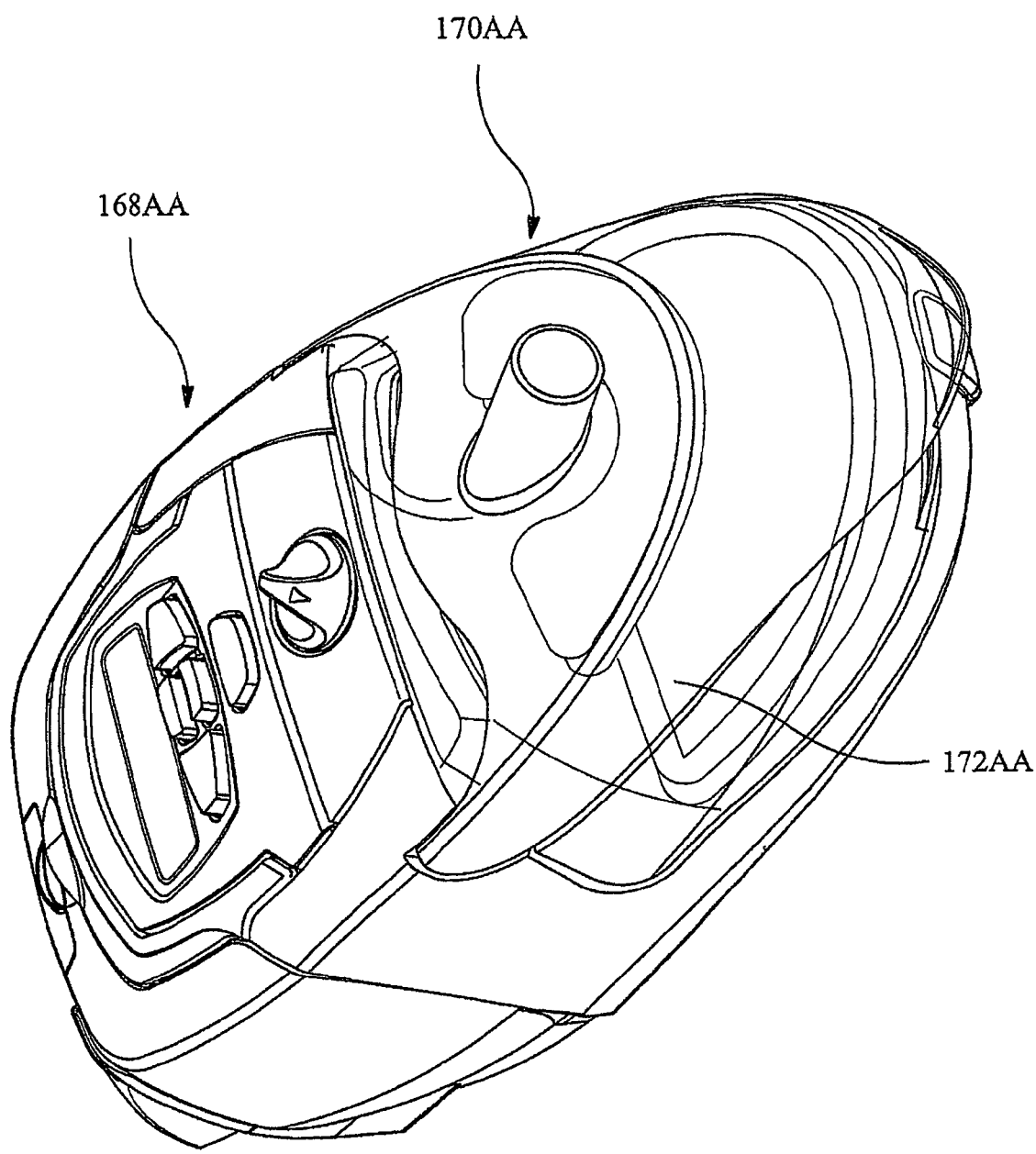
FIG. 41 is a perspective view of a flow generator including a humidifier tub having a lid according to a twenty-sixth embodiment of the present invention.
Figure 42:
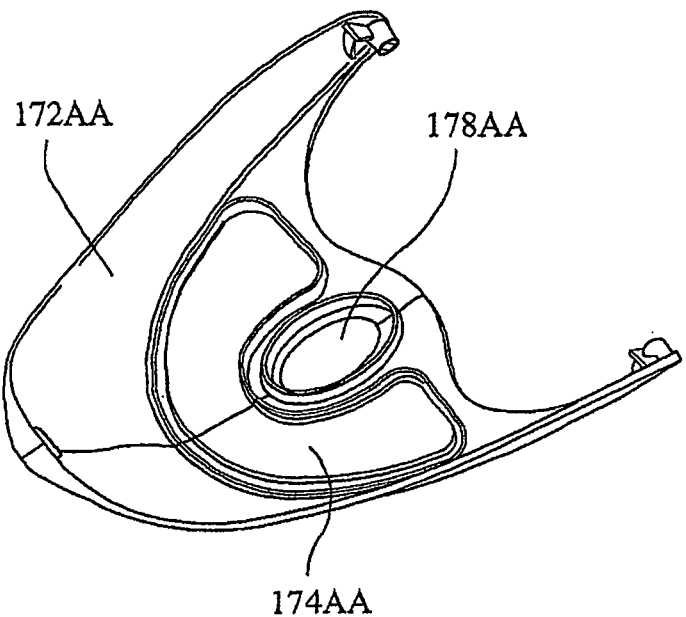
FIG. 42 is a perspective view of the lid of FIG. 41 showing a recess configured to receive a seal.
Figure 43:
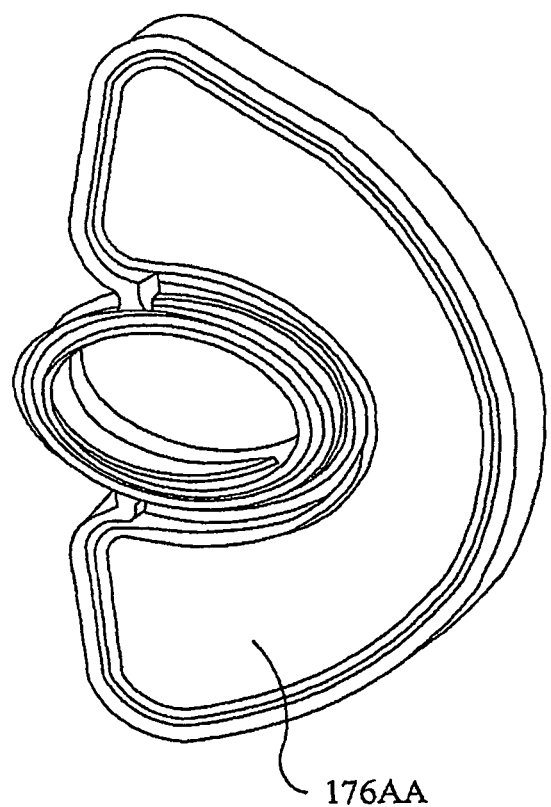
FIG. 43 is a perspective view of a lid seal for the lid of FIG. 41.

U.S. patent application Ser. No. 10/533,940 is incorporated herein by reference in its entirety. Referring to FIGS. 41-43, a ResMed S8 flow generator 168AA is shown comprising a humidifier 170AA. The humidifier 170AA has a lid 172AA, an underside of which is shown in FIG. 42 and includes a recess 174AA. FIG. 43 shows an elastomer seal 176AA that is adapted to fit in the recess 174AA.

The improvement over U.S. patent application Ser. No. 10/533,940 is that the elastomer seal 176AA is co-moulded to the lid 172AA about the air exit aperture 178AA. This overmoulding provides a stronger mounting of the seal 176AA to the lid 172AA than a mere mechanical interlock and also ameliorates the problem of biological growth in crevices. The overmoulding can be in the form of a full surface bond or a peripheral bond.

The improvement ameliorates difficulties sometimes encountered in mounting the seal 176AA on the lid 172AA and makes the step of connecting the two parts during assembly obsolete.

5.11 Elbow-to-Frame Seal

Figure 44:
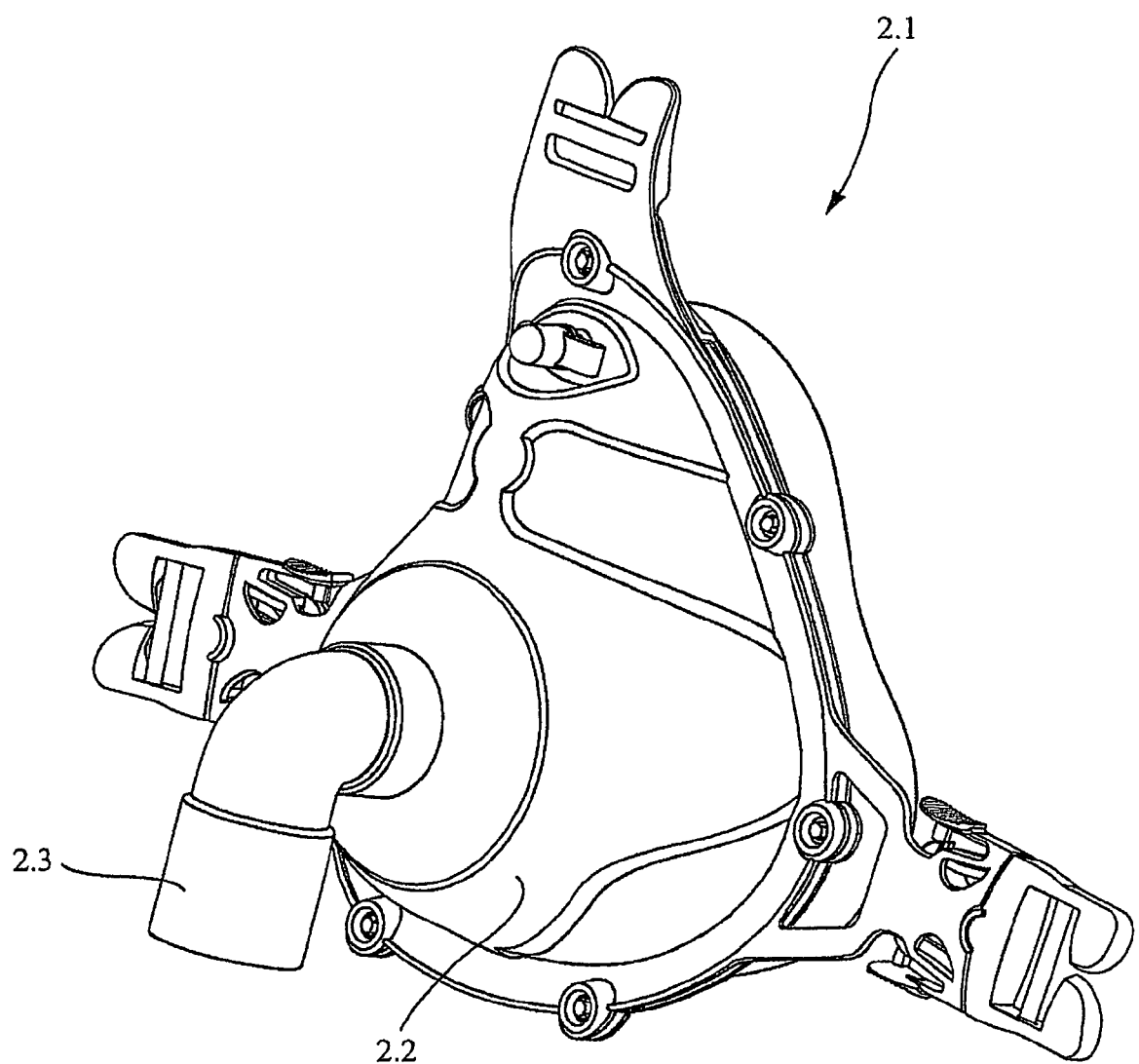
FIG. 44 is a non-vented full face mask according to an embodiment of the present invention.

FIG. 44 shows a full face mask 2.1 having a frame 2.2 and an elbow 2.3 provided to the frame. Details of the overall mask are described in relation to U.S. patent application Ser. No. 11/027,689, filed Jan. 3, 2005, incorporated herein by reference in its entirety. A seal is formed between the elbow and the frame and may be formed on the frame or the elbow using the overmoulding techniques described herein.

Figure 45:
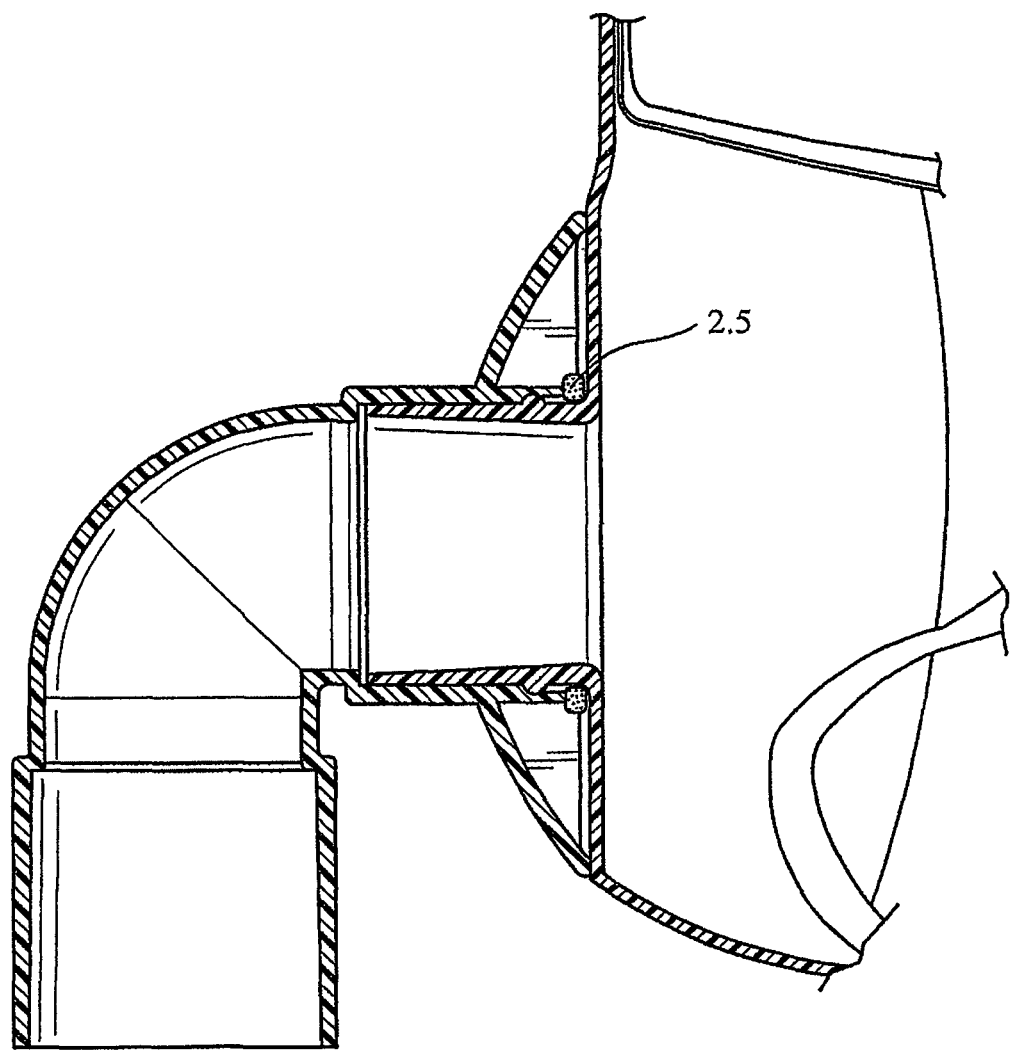
FIG. 45 is a schematic cross-sectional view of a portion of FIG. 44 showing an elbow-to-frame interface/seal according to a first variant.
Figure 46:
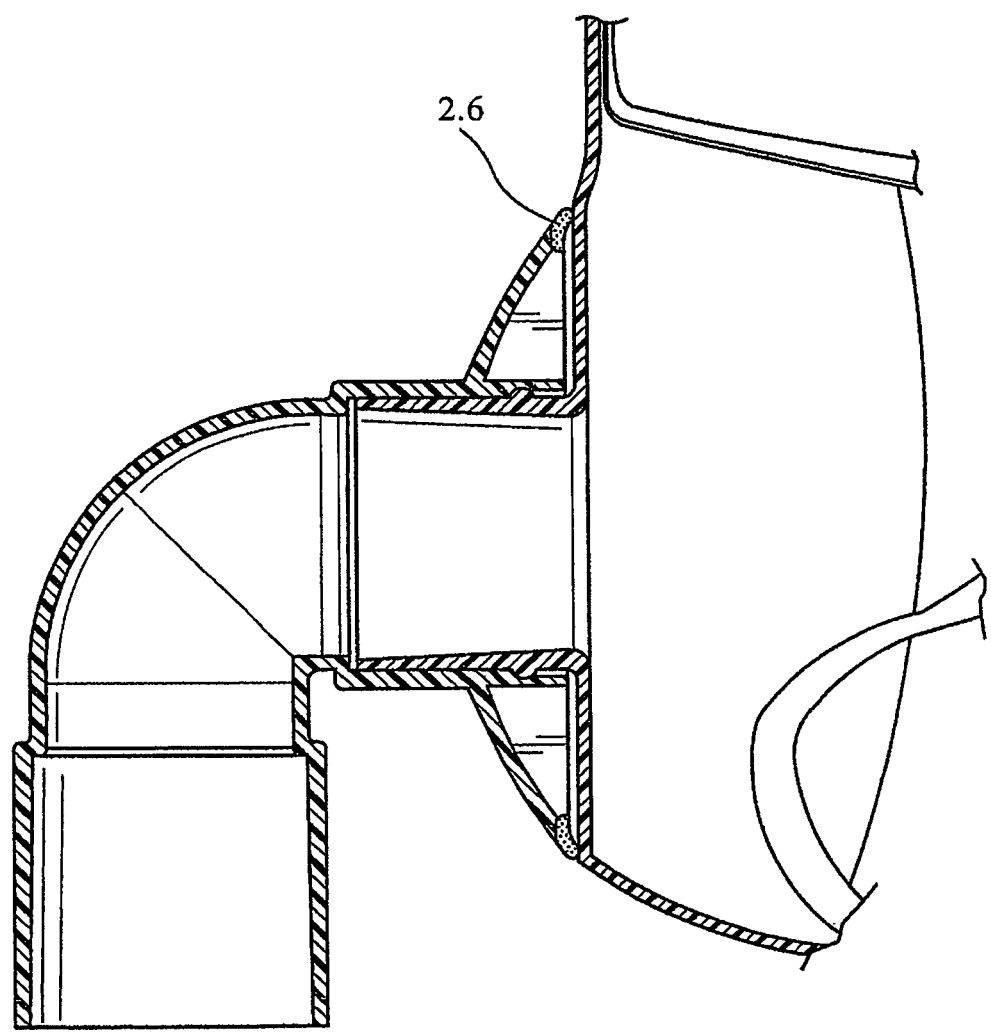
FIG. 46 is a schematic cross-sectional view of a portion of FIG. 44 showing an elbow-to-frame interface/seal according to a second variant.
Figure 47:
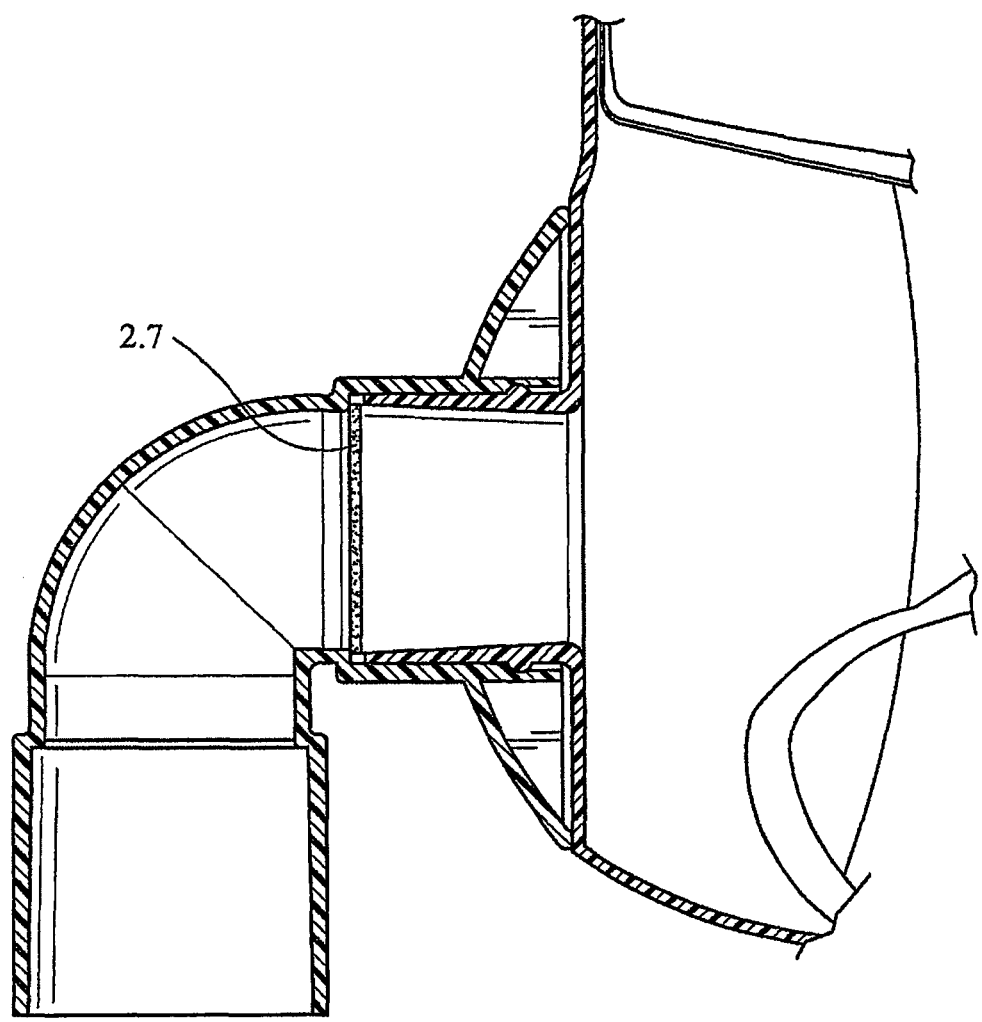
FIG. 47 is a schematic cross-sectional view of a portion of FIG. 44 showing an elbow-to-frame interface/seal according to a third variant.

FIG. 45 shows a seal 2.5 that is formed on an inner circumferential portion of the elbow at the base of the frame inlet. FIG. 46 shows a seal 2.6 formed on an outer circumferential surface of the elbow. FIG. 47 shows a seal 2.7 at the distal end portion of the inlet portion of the frame.

Figure 48:
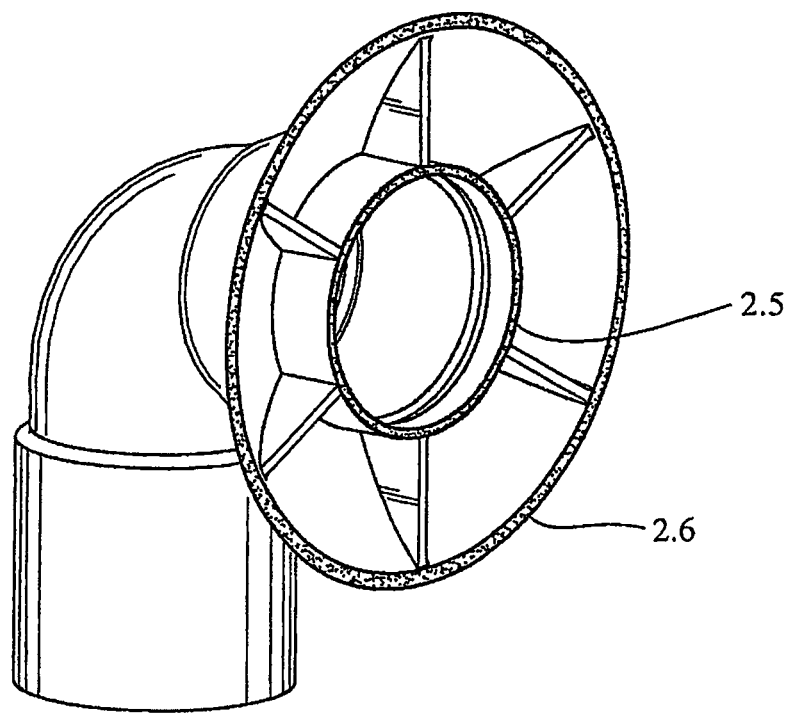
FIG. 48 is a perspective view of an elbow having elastomer seals according to an embodiment of the present invention.

FIG. 48 includes an elbow with the seals from FIGS. 47 and 46 All of the seals 2.5, 2.6 and 2.7 can be formed on either the frame and/or the elbow. The seals help decrease leak while at the same time reduce squeak/squeal if the elbow is rotated relative to the frame.

5.12 Alternative Seal Designs

Figure 49:
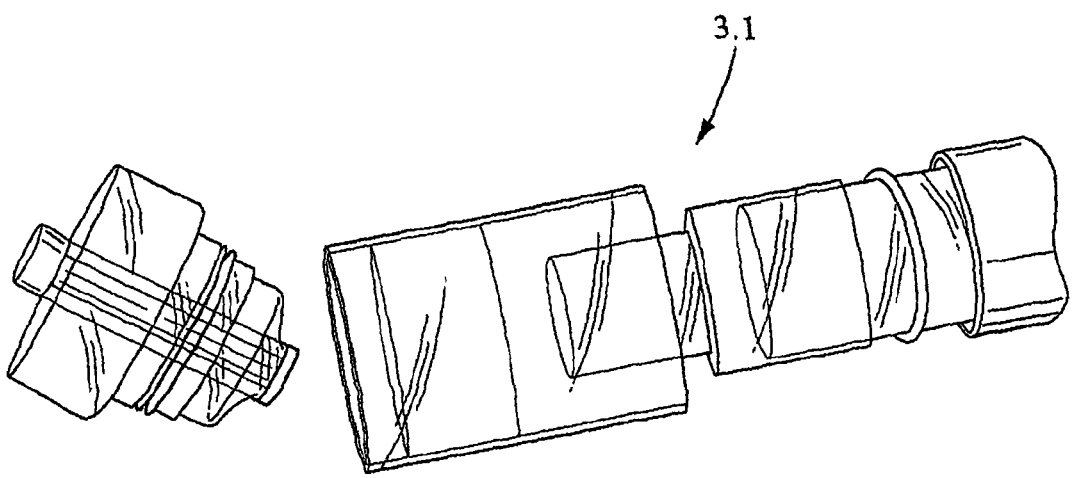
FIG. 49 is an exploded perspective view of a test ring having a seal for insertion within a receptacle according to an embodiment of the present invention.

FIG. 49 is an exploded view of a test rig 3.1 including for testing seals that can be used with the elbow-to-frame connections described above. FIGS. 50-53 illustrate various seal geometries.

Figure 50:
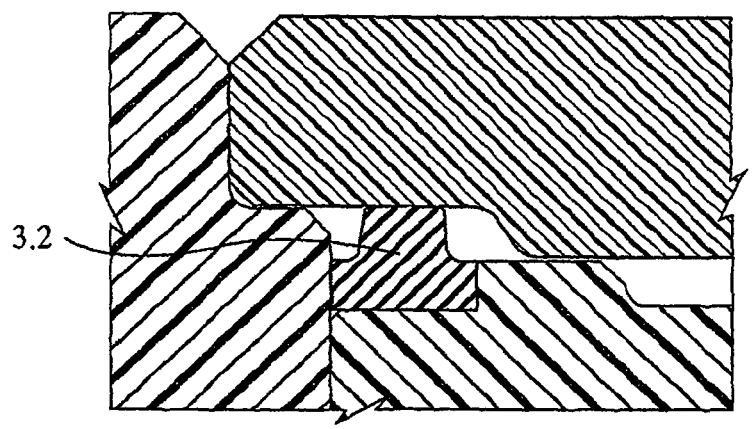
FIGS. 50-53 illustrate partial cross-sectional views of plug seals according to embodiments of the present invention.
Figure 51:
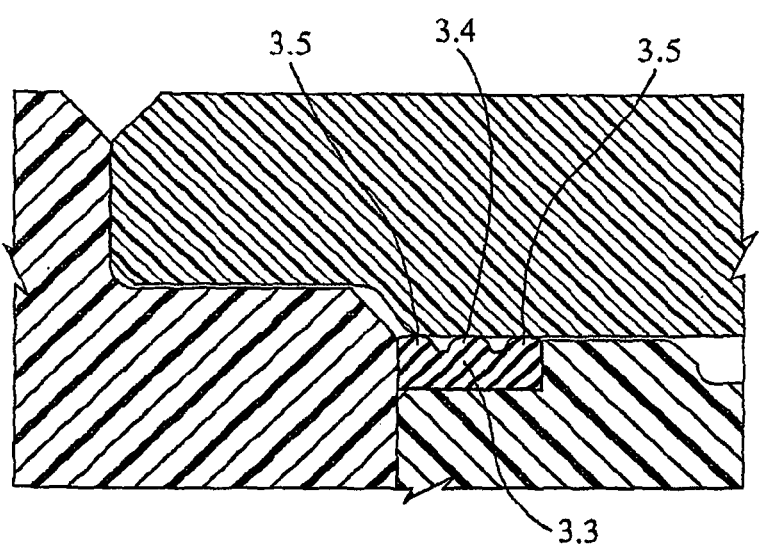
Figure 52:
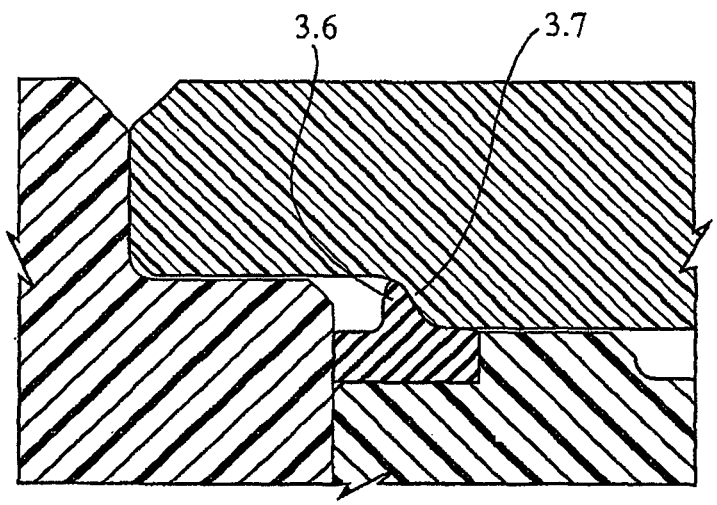
Figure 53:
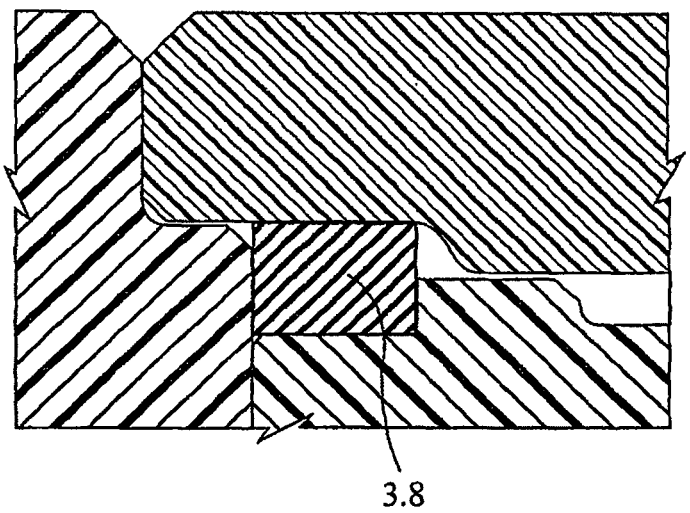

FIG. 50 shows a syringe-type seal 3.2 that is compressed to fit within the bore, but provides high sealing strength. FIG. 51 shows a blade style seal 33. While the main ridge 3.4 contacts the bore, the adjacent portions 3.5 may also contact the bore depending on the desired amount of rotation force required. FIG. 52 shows an axial flap seal 3.6 that engages on an angled face 3.7 of the bore. FIG. 53 shows a rubber seal having a generally rectangular cross-section.

5.13 Mould

Figure 54:
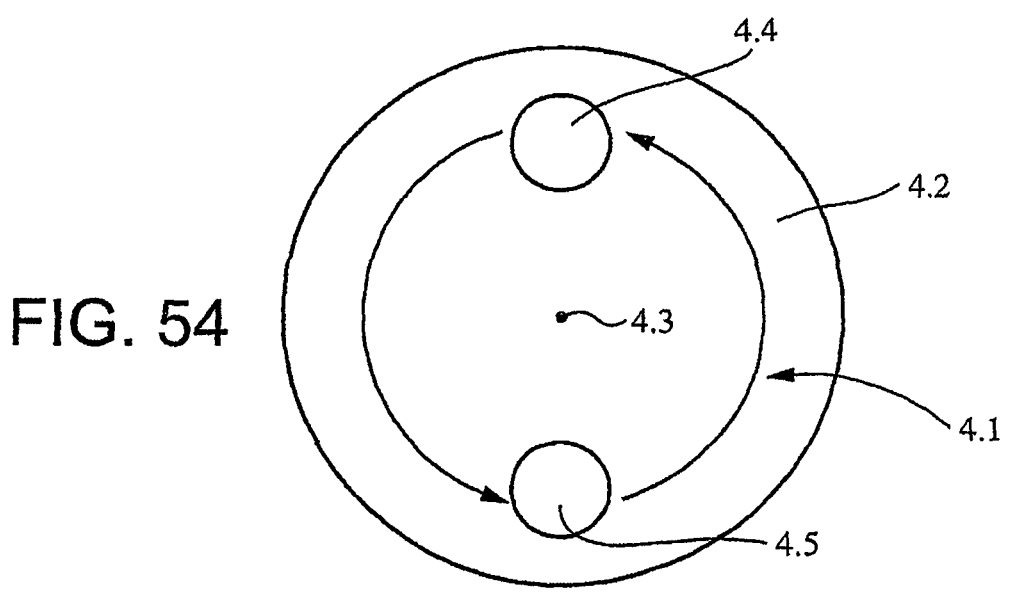
FIG. 54 illustrates a schematic diagram of a mould system according to an embodiment of the present invention.

A mould for a respiratory mask or humidifier tub is provided in one embodiment of this invention. The substantially rigid component mould provides the substantially rigid component with very small sealing rims around the periphery of the elastomer bonding region and the elastomer mould has corresponding notches that form a tortuous path that is difficult for the liquid elastomer or other material to flow through. FIG. 54 shows a sample rotating mould system 4.1 having a turntable 4.2 that rotates about an axis 4.3. Turntable 4.2 includes a first moulding station 4.4 for moulding a first component, e.g., the substrate (e.g., frame) and a second moulding station 4.5 for moulding a second component, e.g., the elastomer (e.g., cushion, pad, seal, etc.).

5.13.1 Mask Design to Facilitate Removal from Mould

The respiratory mask is designed such that its substantially rigid components can be demoulded largely without undercuts. The elastomer components may be made by moulding tool structures that produce undercuts. The demoulding of the elastomer components can then be done by elastic deformation of the elastomer components.

5.14 Fully Automated Mask Manufacture

An automated manufacturing process for a mask is another embodiment of this invention. The automated manufacturing process utilizes overmoulding to manufacture and/or bond appropriate components, in combination with at least one automated assembly step (e.g. fitting the elbow in the socket or attaching the headgear to the headgear clips).

5.15 Advantages 5.15.1 Cost Saving

Overmoulding reduces cost of goods. Components, the only function of which is to hold two other components together are made redundant. Components can also be made from less material when the attachment structure is no longer needed.

To raise an order with a supplier costs money. There is the cost of the labour of the purchasing officer, as well as the cost of transporting each individual part to the company. Overmoulding allows companies to combine two or more components into one, thus significantly reducing the associated purchasing costs.

Overmoulding also reduces inventory costs. These are the costs a company incurs to keep the components in its warehouse and then deliver them to the production floor. In simple terms, half as many parts means half as many transactions. Warehousing staff also have one less part to receive into stores and one fewer part to locate and move.

A mask with less parts also provides further cost savings by reducing the amount of time it takes to assemble the finished product and/or the number of assembly steps. Overmoulding also eliminates secondary operations such as machining and use of adhesives.

5.15.2 Quality Improvement

Improving quality leads to further cost savings. For example, the cost of rework which includes the cost of any materials scrapped, plus the cost of employing a worker to repair or replace a component may be avoided.

An automated overmoulding operation would reduce assembly errors since fewer manual assembly steps are required.

Quality derived through use of overmoulding also reduces costs in terms of reducing disgruntled customers. For example, the often difficult step of assembling a cushion to a frame utilizing a cushion-to-frame clip is avoided.

5.15.3 Sealing

Since flexible materials seal better than harder materials, the use of flexible materials to surface harder materials will allow better seals to be formed. For example, improved sealing between the elbow and frame, and frame and cushion can be achieved.

5.15.4 Soft-Touch

A soft to touch surface generally feels nicer and less clinical than a hard surface to a patient. Varying both the co-mould thickness and hardness can produce a range of different feels.

5.15.5 Biological Contamination can be Removed by Washing

Mask components that have been co-moulded according to some embodiments of the invention can have biological contamination removed therefrom by washing the mask. The reason for this is that the components are integrally joined and thus the mask does not include any crevices that cannot be cleaned within the normal course of washing.

5.16 Materials

Thermoplastic elastomers (TPEs), solid silicone rubbers and Liquid Silicone Rubbers (LSRs) are usually suitable materials for a flexible co-mould. It has been found by the inventors that a thermoplastic elastomer with the following general properties may be particularly advantageous:

Hardness of approximately 40 ShoreA

High Tear strength

Resistance to cleaning chemicals (e.g. soap, detergents etc.)

Low compression set

Ability to withstand cleaning temperatures of 93 degrees Celsius

Low friction and low squeak

Biocompatibility (specifically—ISO 10993, parts 3, 5, 6, 10 & 11)

Good bonding to substantially rigid component

Good process control for high volume manufacture

Translucency

Low cycle time

The following materials have been found to exhibit some or all of the above properties:

"Dynaflex® TPE Compounds" and "Versalloy®" made by GLS

"Santoprene™ Thermoplastic Vulcanizate" and "Santoprene™ Thermoplastic Vulcanizate" made by Advanced Elastomer Systems.

Silastic™ Silicone rubbers made by Dow Corning.

Elastosil™ Silicone rubbers made by Wacker.

Where solid silicone rubbers are used, resin transfer moulding techniques may be used for moulding of the flexible components.

Polycarbonate, polypropylene, trogamid (nylon) and pocan plastics are all suitable substantially rigid materials.

5.17 Other Variations

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. For example, any functionally suitable materials may be utilized in conjunction with this invention. Furthermore, the flexible and substantially rigid materials could have the same level of flexibility or resilience. In another embodiment, the substantially rigid material could be more flexible than the flexible material.

Also, the various embodiments described above may be implemented in conjunction with other embodiments, e.g., aspects of one embodiment may be combined with aspects of another embodiment to realize yet other embodiments, or additional embodiments can reside in a single element or portion thereof of any given embodiment.

In addition, while the invention has particular application to patients who suffer from OSA, it is to be appreciated that patients who suffer from other illnesses (e.g., congestive heart failure, diabetes, morbid obesity, stroke, barriatric surgery, etc.) can derive benefit from the above teachings. Moreover, the above teachings have applicability with patients and non-patients alike in non-medical applications.

The invention claimed is:

1. A respiratory mask for administering a breathable gas to a patient, the respiratory mask comprising
a) a first component formed from an elastomeric material; and
b) a second component formed from a material that is less flexible than the elastomeric material, wherein
the first component is integrally formed onto the second component,
the first component is joined to the second component in both a non-bonded manner and a bonded manner in different places, and
the second component comprises pre-treated places where the first and second components are bonded.

2. The respiratory mask as claimed in claim 1, wherein the first component is manually separable from the second component in the non-bonded places.

3. The respiratory mask as claimed in claim 1, wherein the integral forming is carried out in an injection moulding tool.

4. The respiratory mask as claimed in claim 1, wherein the elastomeric material is a liquid silicone rubber material.

5. The respiratory mask as claimed in claim 1, wherein the second component is formed from a polycarbonate material.

6. The respiratory mask as claimed in claim 1, wherein the first component is a sealing cushion.

7. The respiratory mask as claimed in claim 1, wherein the first component is an outlet conduit device, a forehead-contacting device, a closure device an articulated structure, a diaphragm device, a tubular body portion, a breathing gas line segment, a functional seal, a stop device, a decoration or logo, a headband connection device, or a soft gripping pad.

8. The respiratory mask as claimed in claim 1, wherein the second component is a forehead rest mount, or a mask frame.

9. A mould for a respiratory mask according to claim 1, wherein
the mould comprises a mould cavity in which the first component is moulded onto the second component,
the integral forming is such that the first component is manually separable from the second component in the non-bonded places, and
the integral forming is such that the first component is joined to the second component in a bonded manner in the bonded places.

10. A mould as claimed in claim 9, wherein the mould cavity has a first portion with a shape that substantially matches the shape of the first component and a second portion with a shape that substantially matches the shape of the second component.

11. A mould as claimed in claim 9, wherein the integral forming is carried out in an injection moulding tool.

12. The respiratory mask as claimed in claim 1, wherein the second component comprises pre-treated places only where the first and second component are joined in the bonded manner.

13. A method for manufacturing a respiratory mask, comprising:
providing an elastomeric material for forming into a first component; providing a second component that is less flexible than the elastomeric material in a mould; and
integrally forming the elastomeric material onto the second component within the mould in order to form the first component,
wherein the first component is joined to the second component in both a non-bonded manner and bonded manner, in different places.

14. The method as claimed in claim 13, wherein the first component is manually separable from the second component in the non-bonded places.

15. The method as claimed in claim 13, further comprising pre-treating the second component to strengthen the bond between the first and second components.

16. The method as claimed in claim 15, wherein the pre-treating step comprises applying plasma to a bonding surface of the second component.

17. The method as claimed in claim 16 wherein the plasma is an atmospheric gas plasma.

18. The method as claimed in claim 13, wherein the integral forming is carried out in an injection moulding tool.

19. A respiratory mask for administering a breathable gas to a patient, the respiratory mask comprising:
an elastomeric first component;
a second component that is less flexible than the first component, the first component being molded to the second component, wherein the first and second components are joined together and contact each other at a plurality of contacting places,
wherein the first and second components are releasably joined to each other at a first group of contacting places comprising at least one of the plurality of contacting places, and
wherein the first and second components are permanently joined to each other at a second group of contacting places comprising at least one of the plurality of contacting places.

20. The respiratory mask as claimed in claim 19, wherein the at least one contacting place of the second group of contacting places is pretreated to increase a bonding force between the first and second components.

21. The respiratory mask as claimed in claim 20, wherein the pretreated contacting places are subjected to a plasma treatment.

22. The respiratory mask as claimed in claim 20, wherein the pretreated contacting places are subjected to a corona treatment.

23. The respiratory mask as claimed in claim 20, wherein adhesion promoters are applied to the pretreated contacting places.

24. The respiratory mask as claimed in claim 20, wherein self-adhesive material is applied to the pretreated contacting places and/or non-bonding material is applied to the non-pretreated contacting places.

25. The respiratory mask as claimed in claim 19, wherein the elastomeric material is a liquid silicone rubber material.

26. The respiratory mask as claimed in claim 25, wherein the second component is formed from a polycarbonate material.

27. The respiratory mask as claimed in claim 26, wherein the first component is a sealing cushion.

28. The respiratory mask as claimed in claim 26, wherein the first component is an outlet conduit device, a forehead-contacting device, a closure device an articulated structure, a diaphragm device, a tubular body portion, a breathing gas line segment, a functional seal, a stop device, a decoration or logo, a headband connection device, or a soft gripping pad.

29. The respiratory mask as claimed in claim 26, wherein the second component is a forehead rest mount, or a mask frame.

* * * * *